United States Patent [19]

Caton et al.

[11] 4,088,695

[45] May 9, 1978

[54] CYCLOPENTANONE DERIVATIVES

[75] Inventors: Michael Peter Lear Caton, Upminster; Edward Charles John Coffee, London, both of England; Gordon Leonard Watkins, Santa Monica, Calif.

[73] Assignee: May & Baker Limited, Essex, England

[21] Appl. No.: 543,552

[22] Filed: Jan. 23, 1975

[30] Foreign Application Priority Data

Jan. 26, 1974 United Kingdom ............. 3730/74

[51] Int. Cl.$^2$ ............. C07C 49/76; C07C 49/82; C07C 69/16; C07C 69/78
[52] U.S. Cl. ............. 260/590 C; 560/231; 260/340.9 P; 260/448.2 B; 560/255; 560/107; 560/106; 560/256; 260/586 F; 260/586 R; 260/598; 260/611 R; 424/45; 424/175; 424/275; 424/285; 424/308; 424/311; 424/331; 542/426; 542/429
[58] Field of Search ........ 260/476 R, 476 C, 488 CD, 260/590 C, 240 R

[56] References Cited

U.S. PATENT DOCUMENTS 3,954,881   5/1976   Bowles ............................. 260/590 C

OTHER PUBLICATIONS

Chem. Abstracts, 57: 16427a.
Chem. Abstracts, 61: 13205b.

*Primary Examiner*—Vivian Garner
*Attorney, Agent, or Firm*—Stevens, Davis, Miller & Mosher

[57] ABSTRACT

Cyclopentane derivatives of the formula:

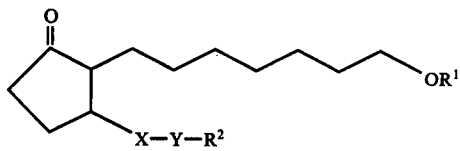

wherein $R^1$ represents hydrogen or a carboxylic acyl group, and either (i) $R^2$ represents a group of the formula:

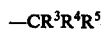

—$CR^3R^4R^5$     II (wherein $R^3$ and $R^4$ represent hydrogen or alkyl, and $R^5$ represents hydrogen, or alkyl, alkoxy, cycloalkyl or adamantyl, or $R^5$ represents alkyl substituted by alkoxy, or by cycloalkyl or by adamantyl, or the group —$CR^3R^4R^5$ together forms a cycloalkyl or adamantyl group), X represents trans-vinylene or ethylene and Y represents carbonyl or a group of the formula:

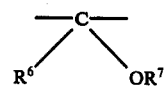

III wherein $R^6$ represents hydrogen or alkyl, and $R^7$ represents hydrogen or a carboxylic acyl group, or else (ii) $R^2$ represents a group of the formula:

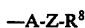

—A-Z-$R^8$     IV (wherein A represents alkylene, Z represents a direct bond or oxygen or sulphur, and $R^8$ represents an aryl or heterocyclyl group which may be substituted by one or more of halogen, alkyl, alkoxy and trihalomethyl), X in formula I represents ethylene or trans-vinylene and Y in formula I represents carbonyl or a group of formula III, or else (iii) $R^2$ represents a group $R^8$ and X and Y in formula I represent simultaneously ethylene and carbonyl, trans-vinylene and carbonyl, or ethylene and —CH($OR^7$)— groups respectively. The compounds are new and possess pharmacological properties similar to those of prostaglandins.

12 Claims, No Drawings

CYCLOPENTANONE DERIVATIVES

This invention relates to new therapeutically useful cyclopentane derivatives, to a process for preparing them, and to pharmaceutical compositions containing them.

The new cyclopentane derivatives of the present invention are those compounds of the general formula:

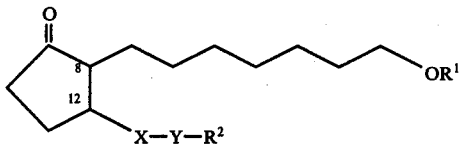

wherein $R^1$ represents a hydrogen atom or a carboxylic acyl group, preferably a straight- or branched-chain alkanoyl group containing from 1 to 4 carbon atoms or a benzoyl group, and either (i) $R^2$ represents a group of the general formula:

$$-CR^3R^4R^5 \quad\quad II$$

(wherein $R^3$ and $R^4$ are identical or different and each represents a hydrogen atom or a straight- or branched-chain alkyl group containing from 1 to 4 carbon atoms, for example a methyl group, $R^5$ represents a hydrogen atom or, preferably, a straight- or branched-chain alkyl group containing from 1 to 10, preferably from 1 to 5, more particularly 4, carbon atoms, a straight- or branched-chain alkoxy group containing from 1 to 10, preferably from 1 to 4, carbon atoms, a cycloalkyl group containing from 5 to 7 carbon atoms, an adamantyl group, or represents a straight- or branched-chain alkyl group containing from 1 to 6 carbon atoms, preferably methyl, substituted by a straight- or branched-chain alkoxy group containing from 1 to 6 carbon atoms, preferably ethoxy, by a cycloalkyl group containing from 5 to 7 carbon atoms or by an adamantyl group, or the group $-CR^3R^4R^5$ together forms a cycloalkyl group containing from 5 to 7 carbon atoms, preferably cyclopentyl or cyclohexyl, or an adamantyl group), X represents a trans-vinylene or an ethylene group, and Y represents a carbonyl group or a group of the general formula:

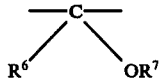

wherein $R^6$ represents a hydrogen atom or a straight- or branched-chain alkyl group containing from 1 to 4 carbon atoms, preferably methyl, and $R^7$ represents a hydrogen atom or a carboxylic acyl group, preferably a straight- or branched-chain alkanoyl group containing from 1 to 4 carbon atoms or a benzoyl group, or else (ii) $R^2$ represents a group of the general formula:

$$-A-Z-R^8 \quad\quad IV$$

[wherein A represents a straight- or branched-alkylene chain containing from 1 to 12, preferably from 1 to 7 carbon atoms, Z represents a direct bond or an oxygen or sulphur atom, and $R^8$ represents an aryl or heterocyclyl group (more particularly a phenyl, naphthyl, furyl or thienyl group), which may be substituted, for example by one or more substituents selected from halogen (e.g. chlorine or bromine) atoms, straight- or branched-chain alkyl and alkoxy groups containing from 1 to 6 carbon atoms, and trihalomethyl, e.g. trifluoromethyl groups], X in formula I represents an ethylene or trans-vinylene group and Y in formula I represents a carbonyl group or a group of formula III (wherein $R^6$ and $R^7$ are as hereinbefore defined), or else (iii) $R^2$ represents a group $R^8$ as hereinbefore defined, and X and Y in formula I represent simultaneously ethylene and carbonyl, trans-vinylene and carbonyl, or ethylene and $-CH(OR^7)-$ groups respectively ($R^7$ being as hereinbefore defined).

As will be apparent to those skilled in the art, the structure shown in general formula I has at least two centres of chirality, these two centres of chirality being at the carbon atoms in positions 8 and 12 respectively. In addition to these two centres of chirality, a further centre of chirality occurs when Y represents a group of formula III and still further centres of chirality may occur in the group $R^2$. The presence of centres of chirality, as is well known, leads to the existence of isomerism. However, the compounds of formula I of the present invention all have such a configuration that the side chains attached to the ring carbon atoms in positions 8 and 12 are trans with respect to each other. Accordingly, all isomers of general formula I, and mixtures thereof, which have those side chains, attached to the ring carbon atoms in positions 8 and 12, in the trans-configuration are within the scope of the present invention. Preferably the groups attached to the 8 and 12 positions of the cyclopentane ring are in the same configuration as those in the natural products known as prostaglandins, viz. alpha and beta respectively.

In the present specification, unless otherwise indicated, alkyl groups are straight- or branched-chain and contain from 1 to 6 carbon atoms.

The compounds of the invention possess valuable pharmacological properties, for example, properties typical of the related series of natural products known as prostaglandins including, for example, the inhibition of gastric acid secretion, the production of hypotension, bronchodilatation, the stimulation of uterine contraction, the production of hypocholesteraemia and hypolipidaemia, and the stimulation of luteolysis.

For example, in laboratory screening tests the compounds produce 50% to 100% inhibition of pentagastrin-induced gastric acid secretion in the rat at doses between 1.0 and 100μg/kg animal body weight/minute when administered orally in solution in dilute aqueous alcohol [containing sodium chloride (about 0.9% w/v) and a small proportion of a wetting agent, e.g. Tween 80, to aid solubility; Tween 80 is a complex mixture of polyoxyethylene ethers of mixed partial oleic esters of sorbitol anhydride]. More particularly, 50% inhibitions of pentagastrin-induced gastric acid secretion were obtained in the rat at a dose of 4.0μg/kg animal body weight/minute of 7-[2-(3-hydroxy-4-methyloct-1-enyl)-5-oxocyclopentyl]heptanol and at a dose of 6/0μg/kg animal body weight/minute of 7-[2-(3-hydroxy-3-methyloct-1-enyl)-5-oxocyclopentyl]heptanol.

In another laboratory test, the effects of aerosols containing compounds of the invention were observed in conscious guinea pigs. Thus, guinea pigs were continuously exposed to an aerosol containing a compound of the invention for a period of 3 minutes. After a pause of 30 seconds, the animals were exposed to an aerosol of the broncho-constrictor histamine generated from a solution of histamine in water (2mg/ml) and the time taken for convulsions to occur (termed the "preconvulsion time") was noted. The concentration of compound of formula I in the solution from which the aerosol was generated which would produce a 100% increase in preconvulsion time was then calculated mathematically from results obtained from solutions of compounds of formula I of various concentrations. For example, it was calculated that the preconvulsion time obtained in animals pre-treated with an aerosol generated from an aqueous solution containing 142μg/ml of 7-[2-(3-hydroxy-4-methyloct-1-enyl)-5-oxocyclopentyl]heptanol, compared with the preconvulsion timed obtained in control animals pre-treated with a similar aerosol from which the compound of the invention was absent, would show an increase of 100% in the preconvulsion time.

In another laboratory test, rats were fed on a diet containing 0.5% w/w cholesterol and 0.25% w/w cholic acid for 7 days. During the last 3 days some of the rats received a daily oral dose of a solution of 7-[2-(3-hydroxy-4-methyloct-1-enyl)-5-oxocyclopentyl]heptanol in a dilute (1% v/v) solution of alcohol in water at a rate of 100μg active compound/kg animal body weight per day, while the other, control, rats received only the aqueous alcohol vehicle. At the end of the 7th day the treated animals had a 33% lower blood cholesterol level and a 43% lower blood triglyceride level, compared with the control animals.

In yet another laboratory test, 7-[2-(3-hydroxy-4-phenoxybut-1-enyl)-5-oxocyclopentyl]heptanol produced luteolysis in more than 50% of pregnant hamsters when administered subcutaneously at a dose of 2mg/kg animal body weight in solution in a dilute (1% v/v) solution of alcohol in water.

As well as the compounds specifically named in the above test descriptions, other compounds of the invention showed useful levels of activity in these and other laboratory tests.

According to a feature of the present invention, compounds of general formula I wherein $R^1$ represents a hydrogen atom, and $R^2$, X and Y are as hereinbefore defined, with the exception of those compounds wherein Y includes a group $—OR^7$ and $R^7$ represents a carboxylic acyl group, are prepared by the process which comprises the acid hydrolysis of compounds of the general formula:

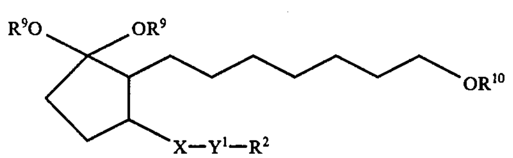

V wherein $R^2$ and X are as hereinbefore defined, $Y^1$ has the same significance as Y as hereinbefore defined with the exclusion of groups of formula III or $—CH(OR^7)—$, wherein $R^7$ in said formulae represents a carboxylic acyl group, the symbols $R^9$ represent identical alkyl groups or together form an ethylene linkage unsubstituted or substituted by identical alkyl groups on each carbon atom, the symbols $R^9$ preferably representing together an unsubstituted ethylene linkage, and $R^{10}$ represents a hydrogen atom, or when $Y^1$ represents a group of formula III wherein $R^6$ represents an alkyl group and $R^7$ represents a hydrogen atom, and group $—OR^{10}$ optionally represents a group, hereinafter represented as $—OR^{11}$, relatively inert to Grignard reagents but readily hydrolysed to a hydroxy group when required, for example $R^{11}$ represents a trimethylsilyl group, and the hydroxy group forming part of the said group of formula III within the definition of $Y^1$ is then optionally in the form of a Grignard intermediate complex, that is to say the said hydroxy group is in a form which may be represented by the formula $—OMgZ^1$, wherein $Z^1$ represents a halogen, e.g. bromine or iodine, atom.

The most suitable reaction conditions for the hydrolysis may readily be determined with a minimum of experimentation, and may vary according to the values of the various symbols in formula V. When the symbol $R^{10}$ represents a group $R^{11}$, and especially when the hydroxy group forming part of the group of formula III is in the form $—OMgZ^1$ the hydrolysis if preferably carried out stepwise, first hydrolysing $—OMgZ^1$ (when present) to hydroxy, then hydrolysing $—OR^{11}$ to hydroxy, then hydrolysing $—C(OR^9)_2—$ to keto, finally isolating the desired compound of formula I. Optionally, but not necessarily, isolation of the hydrolysis product is carried out after each step of the stepwise hydrolysis.

The hydrolysis of $—OMgZ^1$ (when present) to hydroxy is preferably carried out by means of aqueous ammonium chloride solution, preferably below room temperature, e.g. at about 0° C.

The hydrolysis of $—OR^{11}$ to hydroxy without simultaneous hydrolysis of $—C(OR^9)_2—$ to ketone is preferably carried out in a medium of aqueous lower alkanol, e.g. aqueous methanol, preferably in the presence of a small amount of an organic acid, e.g. glacial acetic acid, at room temperature. On the other hand the hydrolysis of $—OR^{11}$ to hydroxy with the sensibly simultaneous hydrolysis of $—C(OR^9)_2—$ to ketone may be carried out in the presence of a larger proportion of organic acid, e.g. acetic acid, and in the absence of alkanol, for example in a mixture of glacial acetic acid and water (about 2:1 v/v), generally at around room temperature.

The hydrolysis of the group $—C(OR^9)_2—$ to ketone is generally carried out by means of an organic acid in the presence of water, for example aqueous acetic acid, e.g. an aqueous acetic acid solution (e.g. 60–99% v/v), or p-toluenesulphonic acid in acetone containing a small amount of water, preferably at temperatures between 5° and 100° C, more particularly between 15° and 30° C, or alternatively by means of a dilute inorganic acid, for example dilute hydrochloric acid, preferably at temperatures between 0° and 100° C, more particularly between 45° and 70° C. As a further alternative the hydrolysis may be effected by subjecting the compound to chromatography, preferably using an eluant containing some organic acid, for example glacial acetic acid. By this means purification is effected simultaneously with hydrolysis.

Compounds of formula I wherein $R^1$ represents a carboxylic acyl group, and those wherein the symbol Y represents a group containing the symbol $R^7$ and wherein $R^7$ represents a carboxylic acyl group, and $R^2$ and X are as hereinbefore defined, are prepared, according to another feature of the invention, by the acylation of corresponding alcohols of formula I by the application or adaptation of known methods, for example by reaction with the appropriate acid anhydride [for example acetic anhydride when $R^1$ and, where applicable, $R^7$ in the desired product represent acetyl group(s)] in the presence of a base, e.g. pyridine, preferably at ambient temperature, optionally in the presence of an inert organic solvent such as an aromatic hydrocarbon (e.g. benzene). It is generally easier to acylate the heptanol chain then it is to acylate the hydroxy group (when present) within the group Y, especially when Y represents a group of formula III wherein $R^6$ represents an alkyl group. Accordingly, when it is desired to acylate a hydroxy group within the group Y as well as to acylate the heptanol chain, more vigorous conditions such as use of a stronger base, or a higher temperature, or the absence of inert organic solvent, or else longer reaction times, are generally selected.

Compounds of formula V wherein X represents a trans-vinylene group, $Y^1$ represents a carbonyl group and $R^{10}$ represents a hydrogen atom, $R^2$ and $R^9$ being as hereinbefore defined, may be prepared by the reaction of compounds of the general formula:

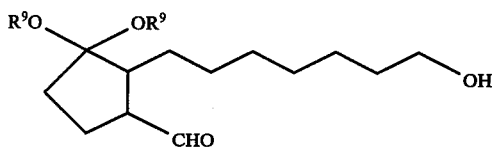

VI (wherein $R^9$ is as hereinbefore defined), either with compounds of the general formula:

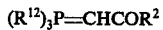

VII (wherein $R^2$ is as hereinbefore defined and $R^{12}$ represents an alkyl group or a phenyl group unsubstituted or substituted by an alkyl group, and advantageously represents a phenyl or n-butyl group), preferably in the presence of an inert organic solvent and preferably at a temperature between 20° and 100° C, for example in the presence of tetrahydrofuran as solvent at the reflux temperature of the reaction mixture or in the presence of hexamethylphosphotriamide as solvent at between 95° and 100° C. or, preferably, with compounds of the general formula:

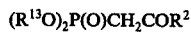

VIII (wherein $R^2$ is as hereinbefore defined and $R^{13}$ represents an alkyl group of from 1 to 4 carbon atoms, preferably a methyl group) in the presence of a strong base, for example sodium hydride, and preferably in the presence of an inert organic solvent, for example an ether (e.g. tetrahydrofuran), and preferably at or near room temperature.

Compounds of formula V wherein either X represents an ethylene group or $Y^1$ represents a hydroxymethylene group, or wherein both X and $Y^1$ respectively have those meanings, $R^2$, $R^9$ and $R^{10}$ being as hereinbefore defined (hereinafter referred to as "compounds of formula Va"), may be prepared by the reduction of compounds of formula V wherein either X represents a trans-vinylene group or $Y^1$ represents a carbonyl group, or wherein both X and $Y^1$ respectively have those meanings, $R^2$, $R^9$ and $R^{10}$ being as hereinbefore defined (hereinafter referred to as "compounds of formula Vb"). Thus:

(a) Compounds of formula Va wherein X represents an ethylene or trans-vinylene group and $Y^1$ represents a hydroxymethylene group may be prepared by reduction of the corresponding compounds of formula Vb wherein X represents an ethylene or trans-vinylene group and $Y^1$ represents a carbonyl group, using means and conditions capable of reducing carbonyl groups to hydroxymethylene groups without affecting carbon-carbon double bonds. The reduction is preferably effected by a metal borohydride (e.g. sodium borohydride or potassium borohydride), usually in an aqueous, alcoholic or aqueous alcoholic medium and at between −40° and +30° C, preferably between −5° and +15° C, optionally in the presence of a base, for example an alkali metal hydroxide (e.g. aqueous sodium hydroxide or aqueous potassium hydroxide) or, especially when potassium borohydride is employed, in aqueous or aqueous alcoholic conditions buffered at a pH of from pH 7 to pH 9, e.g. at pH 8 (e.g. by the addition of aqueous citric acid solution). Alternatively the reduction is carried out by reaction with aluminium isopropoxide, in the presence of isopropanol, preferably as the solvent medium, at an elevated temperature, advantageously at the reflux temperature of the reaction mixture.

(b) Compounds of formula Va wherein X represents an ethylene group and $Y^1$ represents a carbonyl or hydroxymethylene group may be prepared by reduction of the corresponding compounds of formula Vb wherein X represents a trans-vinylene group and $Y^1$ represents a carbonyl or hydroxymethylene group, with means and in conditions capable of reducing carbon-carbon double bonds without affecting carbonyl groups. The reduction is preferably effected by hydrogenation in the presence of a hydrogenation catalyst, for example palladium on charcoal or rhodium on charcoal, in the presence of an inert organic solvent, for example a lower alkanol, e.g. ethanol, generally at ambient temperature and elevated pressure, e.g. at a hydrogen pressure of 15 kilograms per square centimeter.

(c) Compounds of formula Va wherein X represents an ethylene group and $Y^1$ represents a hydroxymethylene group may be prepared by reduction of corresponding compounds of formula Vb with means and in conditions capable of reducing any carbonyl groups present to hydroxymethylene groups and any trans-vinylene groups present to ethylene groups. The reduction is preferably effected by hydrogenation in the presence of a hydrogenation catalyst, for example palladium on charcoal or Raney nickel, in the presence of an inert organic solvent, for example a lower alkanol, e.g. ethanol, preferably at an elevated pressure, e.g. at a hydrogen pressure of 15 kilograms per square centimeter.

Compounds of formula V wherein X represents a trans-vinylene group, $Y^1$ represents a group of formula III wherein $R^6$ represents an alkyl group containing from 1 to 4 carbon atoms and $R^7$ represents a hydrogen atom, $R^2$, $R^9$ and $R^{10}$ being as hereinbefore defined, may be prepared, by means of the Grignard reaction followed by hydrolysis, from compounds of the general formula IX or X:

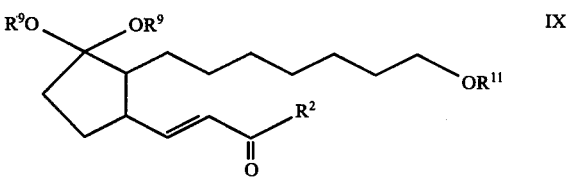

IX

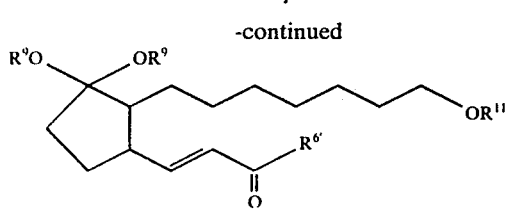

wherein $R^2$, $R^9$ and $R^{11}$ are as hereinbefore defined, and $R^{6'}$ represents a straight- or branched-chain alkyl group containing from 1 to 4 carbon atoms, preferably methyl. The Grignard reagent used may be represented by the general formula XI or XII respectively:

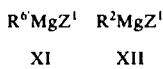

wherein $R^2$, $R^{6'}$ and $Z^1$ are as hereinbefore defined.

The Grignard reaction is carried out in conditions typical of Grignard reactions, for example in an ether (e.g. diethyl ether) at or near room temperature, to form an intermediate of the general formula:

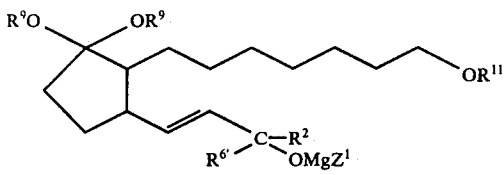

(wherein $R^2$, $R^{6'}$, $R^9$, $R^{11}$ and $Z^1$ are as hereinbefore defined) within general formula V.

As is hereinbefore described, the intermediate compound of formula XIII, generally without isolation, is then converted by hydrolysis to a compound of the general formula:

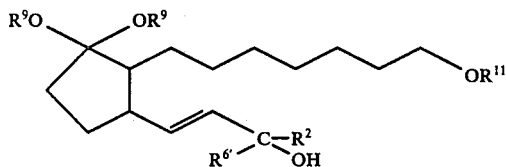

(wherein $R^2$, $R^{6'}$, $R^9$ and $R^{11}$ are as hereinbefore defined) within general formula V which is then hydrolysed to the corresponding compound of formula V wherein $R^{10}$ represents a hydrogen atom, X represents a trans-vinylene group, $Y^1$ represents a group of formula III wherein $R^6$ represents an alkyl group and $R^7$ represents a hydrogen atom, and $R^2$ and $R^9$ are as hereinbefore defined, as is hereinbefore described.

The compounds of formulae IX and X may be prepared from the appropriate alcohols of formula V wherein $R^{10}$ represents a hydrogen atom, X represents a trans-vinylene group, $Y^1$ represents a carbonyl group, and $R^2$ and $R^9$ are as hereinbefore defined, by the application or adaptation of known methods for the introduction of the $R^{11}$ group. When $R^{11}$ represents a trimethylsilyl group, it may be introduced by reaction of the alcohol with hexamethyldisilazane, in the presence of trimethylchlorosilane or hydrogen chloride gas, in dry conditions, for example in dry tetrahydrofuran as solvent.

Compounds of formula V wherein X represents an ethylene group, $Y^1$ represents a group of formula III wherein $R^6$ represents an alkyl group and $R^7$ represents a hydrogen atom, and $R^2$, $R^9$ and $R^{10}$ are as hereinbefore defined, may be prepared by the reduction of corresponding compounds of formula V wherein X represents a trans-vinylene group by the application of methods hereinbefore described for the reduction of carbon-carbon double bonds in compounds of formula V$b$ to form compounds of formula V$a$ wherein X represents an ethylene group.

The compounds of formula VI may be prepared by the reaction sequence which may be illustrated schematically as follows:

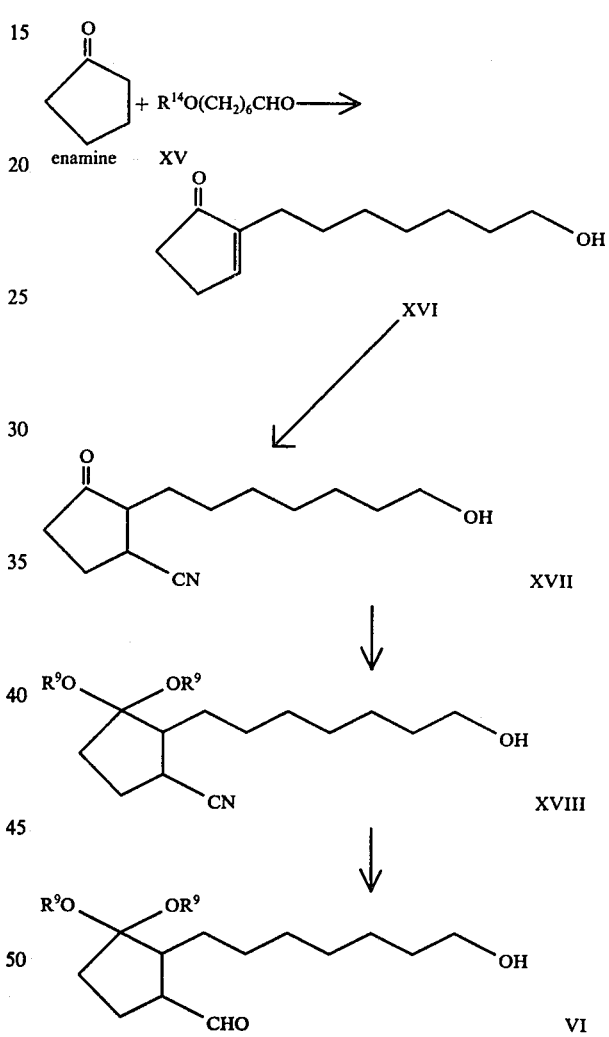

wherein $R^9$ is as hereinbefore defined and $R^{14}$ represents a hydrogen atom or a suitable acid labile group. Suitable acid labile groups represented by $R^{14}$ are those which are easily removed by acid hydrolysis and do not cause side reactions, e.g. the 2-tetrahydropyranyl group unsubstituted or substituted by, for example, at least one lower alkyl group.

The reaction of an aldehyde of formula XV and an enamine (e.g. the morpholine enamine) of cyclopentanone to yield an alcohol of formula XVI is carried out in an inert organic solvent, for example an aromatic hydrocarbon (e.g. benzene) with continuous removal of water, preferably at 60°–120° C., followed by hyrolysis in aqueous acid conditions (e.g. with hydrochloric acid), preferably at ambient temperature, and then heating with an acid (e.g. concentrated hydrochloric acid), preferably at about 100° C., and preferably in an inert organic solvent such as an alcohol (e.g. butanol) to cause the double bond to migrate from the exocyclic to the endocyclic position.

The alcohols of general formula XVI are reacted with a source of hydrogen cyanide (e.g. acetone cyanohydrin) preferably in the presence of a base, for example an alkali metal carbonate (e.g. sodium carbonate), in an aqueous organic solvent, for example an aqueous lower alkanol (e.g. aqueous methanol), preferably at 50°–110° C. and advantageously at the reflux temperature of the solvent employed, to give ketonitriles of formula XVII.

The ketals of general formula XVIII are prepared from the ketonitriles of formula XVII by the application or adaptation of known methods for the preparation of ketals from ketones, for example by the reaction of a compound of formula XVII with the appropriate alcohol or diol in the presence of an acidic catalyst, for example p-toluenesulphonic acid, with continuous removal of water. Advantageously the reaction is effected in the presence of an inert organic solvent, for example an aromatic hydrocarbon (e.g. benzene), at an elevated temperature, with the continuous removal of water by means of a Dean and Stark apparatus.

The ketals of general formula XVIII are reduced in an inert organic solvent, for example a lower dialkyl ether (e.g. diethyl ether), preferably at a temperature between −80° C. and +30° C., to compounds of formula VI by means of known complex metal reducing agents, preferably a dialkylaluminium hydride (e.g. diisobutylaluminium hydride) in an inert organic solvent, for example an aromatic hydrocarbon (e.g. benzene).

The enamines of cyclopentanone used as initial starting materials in the process of preparation of the compounds of formula VI may be prepared from cyclopentanone and secondary amines, preferably in an aromatic hydrocarbon solvent (e.g. benzene or toluene), by the method of G. Stork et al, J. Am. Chem. Soc., 1963, 85, 207. Preferred secondary amines are 5- or 6-membered nitrogen-containing secondary heterocyclic bases, which may carry in the ring one or two additional hetero atoms selected from oxygen and nitrogen (e.g. morpholine). When the amine contains more than one nitrogen atom, one of the nitrogen atoms is secondary and the remainder are tertiary.

By the term "known methods" as used in this specification is meant methods heretofore used or described in the literature.

As will be readily appreciated by those skilled in the art, the isomeric forms of the compounds of the invention arising from the aforementioned centres of chirality may be separated by the application or adaptation of known methods, for example diastereoisomeric forms may be separated by chromatography using selective adsorption from solution or from the vapour phase onto suitable adsorbents, or by fractional crystallisation from suitable solvent systems.

Preferred compounds of the present invention are the compounds within formula I as hereinbefore defined and wherein one or more of the following conditions applies:

(a) Y represents a group of formula III wherein $R^6$ represents a methyl group;

(b) $R^2$ represents a group of formula II wherein $R^4$ represents a methyl group;

(c) $R^2$ represents a phenoxymethyl group.

Compounds of particular importance are the following:

7-[2-(3-hydroxy-3-methyloct-1-enyl)-5-oxocyclopentyl]heptanol,

7-[2-(3-hydroxy-4-phenoxybut-1-enyl)-5-oxocyclopentyl]heptanol,

7-[2-(3-hydroxy-3-methyl-4-phenoxybut-1-enyl)-5-oxocyclopentyl]heptanol,

7-[2-(4-methyl-3-oxooct-1-enyl)-5-oxocyclopentyl]heptanol and

7-[2-(3-hydroxy-4-methyloct-1-enyl)-5-oxocyclopentyl]heptanol.

The following Examples illustrate the compounds of the present invention and their preparation.

EXAMPLE 1

7-[2-(4-Methyl-3-oxooct-1-enyl)-5-oxocyclopentyl]heptanol (i) Preparation of 2-(7-hydroxyheptyl)cyclopent-2-en-1-one A mixture of 7-(2-tetrahydropyranyloxy)heptanal (22 g.) and 1-morpholinocyclopentene, i.e. the morpholine enamine of cyclopentanone, (21.4 g.) in benzene (25 ml.) was heated under reflux for 12 hours under nitrogen, and the water liberated was continuously removed with a Dean and Stark head. Benzene (10 ml.) and then, dropwise, 18% hydrochloric acid (28 ml.) were added and the mixture was stirred for 2 hours. The organic layer was separated and evaporated. Concentrated hydrochloric acid (72 ml.) and butanol (300 ml.) were added to the residue. The mixture was heated at 100° C. for 1 hour, and then the solution was concentrated to give an oil. Diethyl ether was added, and the ether solution was washed with aqueous sodium bicarbonate and then water, and dried over sodium sulphate. The solvent was evaporated and the residue was distilled under reduced pressure to give 2-(7-hydroxyheptyl)cyclopent-2-en-1-one (11.7 g.), b.p. 125°–170° C/0.15 mm.Hg, $n_D^{25}$1.490, $\mu_{max}$228m$\mu$ (ethanol).

The 7-(2-tetrahydropyranyloxy)heptanal used as starting material in the above procedure was prepared as follows:

3,4-Dihydro-2H-pyran (272 g.) was added dropwise at 40° C. with stirring to a mixture of 7-hydroxyheptanenitrile (284 g.) and concentrated hydrochloric acid (10 drops). The temperature was allowed to rise to 65° C. and was maintained at this level for one hour. The solution was cooled and benzene (500 ml.) was added. The solution was washed with aqueous sodium bicarbonate and then water, and dried over sodium sulphate. The solvent was removed in vacuo, and the residue distilled under reduced pressure to give 7-(2-tetrahydropyranyloxy)heptanenitrile (411 g.), b.p. 100°–130° C./0.1 mm.Hg, $n_D^{25}$1.455.

Diisobutylaluminium hydride (19.4 g.) in dry benzene (50 ml.) was added dropwise at 10° C. to a stirred solution of 7-(2-tetrahydropyranyloxy)heptanenitrile (20.6 g.) in dry diethyl ether (200 ml.). The solution was stirred at 10° C. for 30 minutes and was then added to 2N aqueous sulphuric acid (300 ml.) at 0° C. The mixture was heated at 30° C. for 30 minutes, and then saturated with sodium chloride and the layers were separated. The aqueous layer was extracted with diethyl ether and the combined organic layers were washed with aqueous sodium bicarbonate, and then aqueous sodium chloride, and dried over sodium sulphate. The solvent was evaporated and the residue was distilled under reduced pressure to give 7-(2-tetrahydropyranyloxy)heptanal (12.7 g.), b.p. 78°–106° C./0.1 mm.Hg, $n_D^{25}$ 1.456.

The above procedure may also be carried out replacing the 7-(2-tetrahydropyranyloxy)heptanal by 7-hydroxyheptanal [prepared as described above for 7-(2-tetrahydropyranyloxy)heptanal, but using 7-hydroxyheptanenitrile in place of 7-(2-tetrahydropyranyloxy)heptanenitrile].

Advantageously 7-hydroxyheptanal can be prepared in one step from aleuritic acid using the method described below.

Sodium hydroxide (13.2 g.) in water (660 ml.) was added to aleuritic acid (100 g.)and the suspension stirred at 0° to 10° C. To the resulting suspension of sodium aleuritate was added sodium periodate (80 g.) in water (800 ml.) over 1 hour, without allowing the temperature to rise above 15° C. Dichloromethane (200 ml.) was then added and the mixture stirred for a further 2.5 hours at 15° C. A further amount of dichloromethane (300 ml.) and saturated aqueous sodium bicarbonate (100 ml.) were added and the mixture vigorously stirred. The precipitated sodium iodate was removed by filtration and the dichloromethane layer separated. The aqueous phase was washed with dichloromethane (500 ml.) and the combined dichloromethane extracts dried over anhydrous magnesium sulphate. Removal of the dichloromethane in vacuo below 40° C. gave 7-hydroxyheptanal (43 g.), $\nu_{max}$ 3400 cm$^{-1}$, 2700 cm$^{-1}$, 1710 cm$^{-1}$.

(ii) Preparation of 2-(7-hydroxyheptyl)-3-oxocyclopentanecarbonitrile

A mixture of 2-(7-hydroxyheptyl)cyclopent-2-en-1-one (17 g.), acetone cyanohydrin (8.5 g.), 6% aqueous sodium carbonate (8 ml.) and methanol (50 ml.) was stirred and heated under reflux for 4 hours. Methanol was removed in vacuo, water (100 ml.) was added and the mixture was extracted with diethyl ether and dried over magnesium sulphate. The solvent was removed by evaporation, and the residue was distilled under reduced pressure to give 2-(7-hydroxyheptyl)-3-oxocyclopentanecarbonitrile (13.3 g.), b.p. 144°–182° C./0.15 mm.Hg, $n_D^{25}$ 1.4795.

(iii) Preparation of 7-cyano-6-(7-hydroxyheptyl)-1,4-dioxaspiro[4,4]nonane

A mixture of 2-(7-hydroxyheptyl)-3-oxocyclopentanecarbonitrile (20 g.), ethylene glycol (5.6 g.), p-toluenesulphonic acid (1 g.) and benzene (160 ml.) was heated to reflux for 3½ hours with continuous removal of water. The mixture was cooled to ambient temperature, anhydrous sodium carbonate was added, and after filtration through a bed of sodium carbonate, the solvent was removed under reduced pressure. The residue was distilled under reduced pressure to give 7-cyano-6-(7-hydroxyheptyl)-1,4-dioxaspiro[4,4]nonane (19.3 g.), b.p. 166°–182° C./0.1 mm.Hg. This material was used as a starting material in the next stage, an aliquot being redistilled to b.p. 177°–179° C./0.1 mm.Hg for elemental analysis:

Found: C, 67.1; H, 9.2; N, 4.89%; $C_{15}H_{25}NO_3$ requires: C, 67.37; H, 9.42; N, 5.24%.

(iv) Preparation of 7-formyl-6-(7-hydroxyheptyl)-1,4-dioxaspiro[4,4]nonane

A solution of diisobutylaluminium hydride (53 g.) in dry benzene (145 ml.) was added, with rapid stirring, to a solution of 7-cyano-6-(7-hydroxyheptyl)-1,4-dioxaspiro[4,4]nonane (43.2 g.) in dry diethyl ether (432 ml.) at 10°–15° C. Stirring at ambient temperature was continued for 1½ hours and the mixture was added to 2N aqueous acetic acid (1 liter) at a temperature lower than 15° C. The organic phase was separated and the aqueous layer was extracted with diethyl ether. The combined organic phases were washed with aqueous sodium bicarbonate, dried over sodium sulphate, the solvents removed in vacuo and the residue distilled under reduced pressure to give 7-formyl-6-(7-hydroxyheptyl)-1,4-dioxaspiro[4,4]nonane (25.3 g.), b.p. 164°–200° C./0.04–0.05 mm.Hg, $\nu_{max}$ 1710 cm$^{-1}$, 2700 cm$^{-1}$ (liquid film).

(v) Preparation of 6-(7-hydroxyheptyl)-7-(4-methyl-3-oxooct-1-enyl)-1,4-dioxaspiro[4,4]nonane A mixture of 7-formyl-6-(7-hydroxyphptyl)-1,4-dioxaspiro[4,4]nonane (3.88 g.) and 2-methylhexanoylmethylenetriphenylphosphoran (6.0 g.) in dry tetrahydrofuran (30 ml.) was heated to reflux under nitrogen for 18 hours. The solvent was removed in vacuo and the residue triturated with petroleum ether (b.p. 60°–80° C.), allowed to stand at 0° C., filtered to remove triphenylphosphine oxide and the filtrate evaporated to give 6-(7-hydroxyheptyl)-7-(4-methyl-3-oxooct-1-enyl)-1,4-dioxaspiro[4,4]nonane (5.56 g.), $\nu_{max}$ 1620 cm$^{-1}$, 1660 cm$^{-1}$.

2-Methylhexanoylmethylenetriphenylphosphorane, used as a starting material, was prepared as follows:

A solution of 1-chloro-3-methylheptan-2-one (49.4 g.) and triphenylphosphine (79.5 g.) in chloroform (250 ml.) was saturated with nitrogen and refluxed under nitrogen overnight. The chloroform was removed in vacuo and the residue (crude 3-methyl-2-oxoheptyltriphenylphosphonium chloride) was added portionwise to a solution of sodium carbonate (109 g.) in water (1500 ml.) and the mixture was stirred vigorously for 24 hours. The solution was extracted with diethyl ether, and the ethereal extracts were dried over magnesium sulphate. The solvent was removed by evaporation and the residue was cooled and triturated with petroleum ether (b.p. 60°–80° C.) to give 2-methylhexanoylmethylenetriphenylphosphorane (35.2 g.), m.p. 107°–109° C.

1-Chloro-3-methylheptan-2-one, used as starting material, was prepared as follows:

2-Methylhexanoyl chloride (42.5 g.) was added dropwise at −40° C. to a solution of diazomethane (24 g.) in diethyl ether (600 ml.) and the solution was stirred for 1 hour at ambient temperature. Hydrogen chloride gas was then bubbled into the solution until it was fully saturated. Crushed ice was added to give approximately 1 liter of aqueous solution. The organic layer was separated and the aqueous layer was extracted with diethyl ether. The combined organic layers were dried over magnesium sulphate, evaporated, and the residue distilled under reduced pressure to give 1-chloro-3-methyl-yl-heptan-2-one (49.5 g.), b.p. 100°–110° C./13 mm.Hg.

As an alternative method for the preparation of 6-(7-hydroxyheptyl)-7-(4-methyl-3-oxooct-1-enyl)-1,4-dioxaspiro[4,4]nonane, the following procedure was followed:

Dimethyl 3-methyl-2-oxoheptylphosphonate (5.1 g.; prepared as described in the Specification of Netherlands Patent Application No. 7203126) in dry tetrahydrofuran (20 ml.) was added dropwise to a stirred suspension of sodium hydride (0.52 g.) in dry tetrahydrofuran (150 ml.) at ambient temperature under nitrogen. The reaction mixture was stirred at ambient temperature until hydrogen evolution had ceased, and then treated with a solution of 7-formyl-6-(7-hydroxyheptyl)-1,4-dioxaspiro[4,4]nonane (5.1 g.) in dry tetrahydrofuran (50 ml.). After stirring for a further period of 2 hours at ambient temperature the reaction mixture was acidified to pH 4 with glacial acetic acid and then concentrated under reduced pressure. The residue was triturated with diethyl ether and filtered. The filtrate was washed with dilute aqueous sodium carbonate solution and water respectively, then dried over sodium sulphate. Removal of the solvent under reduced pressure gave crude 6-(7-hydroxyheptyl)-7-(4-methyl-3-oxooct-1-enyl)-1,4-dioxaspiro[4,4]nonane (7.6 g.), $\nu_{max}$ (liquid film) 3450 cm$^{-1}$, 1680 cm$^{-1}$, 1660 cm$^{-1}$, 1620 cm$^{-1}$, 1380 cm$^{-1}$, 1040 cm$^{-1}$, which was used in the next stage without further purification being necessary.

(vi) Preparation of
7-[2-(4-methyl-3-oxooct-1-enyl)-5-oxocyclopentyl]heptanol

A mixture of 6-(7-hydroxyheptyl)-7-(4-methyl-3-oxooct-1-enyl)-1,4-dioxaspiro[4,4]nonane (1.0 g.) and hydrochloric acid (25 ml; 1N) was stirred at 60° C. for 2 hours, cooled to ambient temperature and extracted with diethyl ether. The ether extract was washed with 2N aqueous sodium carbonate solution and water respectively then dried over magnesium sulphate. Removal of the solvent under reduced pressure gave a crude product (0.7 g.) which was purified by preparative thin layer chromatography on silica gel, using a mixture of diethyl ether, ethyl acetate and hexane (2:1:1 v/v) as eluant, to give 7-[2-(4-methyl-3-oxooct-1-enyl)-5-oxocyclopentyl]heptanol (0.38 g.), $\nu_{max}$ (liquid film) 3450 cm$^{-1}$, 1730 cm$^{-1}$, 1690 cm$^{-1}$, 1660 cm$^{-1}$, 1380 cm$^{-1}$, 995 cm$^{-1}$; $\lambda_{max}$ (ethanol) 230 nm ($\epsilon$ = 13,600); Elemental analysis: Found: C, 74.9; H, 11.0%; $C_{21}H_{36}O_3$ requires C, 74.95; H, 10.8%; N.M.R. (approximately 10% solution in deuterochloroform): Triplets at 3.57 δ (J = 6 cycles/sec.) and 0.88 δ, doublet of doublets at 6.81 δ (J = 15.5 cycles/sec. and J = 7 cycles/sec.), doublets at 6.20 δ (J = 15.5 cycles/sec.) and 1.11 δ (J = 7 cycles/sec.), broad singlet 2.0 δ.

EXAMPLE 2

7-[2-(3-Hydroxy-4-methyloct-1-enyl)-5-oxocyclopentyl]heptanol (i) Preparation of
6-(7-hydroxyheptyl)-7-(3-hydroxy-4-methyloct-1-enyl)-1,4-dioxaspiro[4,4]nonane 6-(7-Hydroxyheptyl)-7-(4-methyl-3-oxooct-1-enyl)-1,4-dioxaspiro[4,4]nonane [1.0 g.; prepared as hereinbefore described in Example 1 (v)] was dissolved in methanol (50 ml.) and added to aqueous sodium citrate solution (130 ml.; 2% w/v. To this stirred solution, at −5° to 0° C, solid potassium borohydride (2.24 g.) was added portionwise at such a rate as to avoid undue effervescence and the reaction mixture was maintained at pH 8 by the occasional addition of aqueous citric acid solution (10% w/v). After the final addition of the potassium borohydride the reaction mixture was stirred at −5° to 0° C. and pH 8 for 90 minutes. Acetone (50 ml.) was then added, the solution was saturated with sodium chloride, and extracted with diethyl ether. The combined ether extracts were washed with a saturated solution of sodium chloride in hydrochloric acid (2N) and saturated sodium chloride solution respectively, then dried over sodium sulphate. Removal of the solvent under reduced pressure gave crude 6-(7-hydroxyheptyl)-7-(3-hydroxy-4-methyloct-1-enyl)-1,4-dioxaspiro[4,4]nonane (0.6 g.), $\nu_{max}$ 3400 cm$^{-1}$, 1040 cm$^{-1}$, 970 cm$^{-1}$, which was used in the next stage without further purification.

(ii) Preparation of
7-[2-(3-hydroxy-4-methyloct-1-enyl)-5-oxocyclopentyl]heptanol.

A mixture of crude 6-(7-hydroxyheptyl)-7-(3-hydroxy-4-methyloct-1-enyl)-1,4-dioxaspiro[4,4]nonane (0.5 g.) and hydrochloric acid (50 ml; 2N) was stirred at 60° C. for 2 hours, cooled to ambient temperature and then extracted with diethyl ether. The ether extract was washed with water and dried over magnesium sulphate. Removal of the solvent under reduced pressure gave a crude product (0.4 g.) which was purified by preparative thin layer chromatography on silica gel, using a mixture of diethyl ether, ethyl acetate and hexane (2:1:1 v/v) as eluant, to give 7-[2-(3-hydroxy-4-methyloct-1-enyl)-5-oxocyclopentyl]heptanol (0.15 g.), $\nu_{max}$ 3400 cm$^{-1}$, 1725 cm$^{-1}$, 970 cm$^{-1}$; Elemental analysis: Found C, 74.8; H, 11.7%; $C_{21}H_{38}O_3$ requires C, 74.5; H, 11.53%; N.M.R. (approximately 10% solution in deuterochloroform): multiplets at 5.7–5.5 δ, 3.98 δ and 1.05–0.7 δ, triplet at 3.6 δ (J = 6 cycles/sec.), based singlet at 2.05 δ.

EXAMPLE 3

7-[2-(3-Hydroxy-3-methyloct-1-enyl)-5-oxocyclopentyl]heptanol (i) Preparation of
6-(7-hydroxyheptyl)-7-(3-oxooct-1-enyl)-1,4-dioxaspiro[4,4]nonane A mixture of 7-formyl-6-(7-hydroxyheptyl)-1,4-dioxaspiro[4,4]nonane [6 g; prepared as hereinbefore described in Example 1(iv)] and hexanoylmethylenetriphenylphosphorane (8.5 g.) in dry tetrahydrofuran (50 ml.) was heated to reflux under nitrogen for 16 hours. The solvent was removed in vacuo and the residue triturated with petroleum ether (b.p. 60°–80° C.), cooled to 0° C. for 1 day, filtered to remove triphenylphosphine oxide and the filtrate evaporated. The residue was again triturated with petroleum ether (b.p. 60°–80° C.) to remove further triphenylphosphine oxide, filtered, and evaporated to give 6-(7-hydroxyheptyl)-7-(3-oxooct-1-enyl)-1,4-dioxaspiro[4,4]nonane (7.5 g.), $\nu_{max}$ 1620 cm$^{-1}$, 1660 cm$^{-1}$.

Hexanoylmethylenetriphenylphosphorane, used as starting material, was prepared as follows:

A solution of 1-chloroheptan-2-one (33 g.) and triphenylphosphine (60 g.) in chloroform (50 ml.) was saturated with nitrogen and refluxed under nitrogen overnight. The chloroform was removed in vacuo and the residue was dissolved in dichloromethane (150 ml.). Dry diethyl ether (600 ml.) was added to precipitate 2-oxoheptyltriphenylphosphonium chloride (60 g.), m.p. 165°–168° C. This compound (23 g.) was added portionwise to a solution of sodium carbonate (25 g.) in water (250 ml.) and the mixture was stirred vigorously for 24 hours. The solution was extracted with diethyl ether, and the ethereal extracts were dried over magnesium sulphate. The solvent was removed by evaporation and the residue was cooled and triturated with petroleum ether (b.p. 40°–60° C). The solid thus obtained was recrystallised from petroleum ether (b.p. 60°–80° C.) to give hexanoylmethylenetriphenylphosphorane (17 g.), m.p. 73°–74° C.

(ii) Preparation of 6-(7-trimethylsilyloxyheptyl)-7-(3-oxooct-1-enyl)-1,4-dioxaspiro[4,4]nonane.

Hexamethyldisilazane (7.5 ml.) and trimethylchlorosilane (1.5 ml.) were added to a stirred solution of 6-(7-hydroxyheptyl)-7-(3-oxooct-1-enyl)-1,4-dioxaspiro[4,4]nonane (2.0 g.) in dry tetrahydrofuran (100 ml.) and the mixture was stirred at room temperature for 24 hours. The mixture was then filtered and the solvent was removed from the filtrate in vacuo. Xylene (20 ml.) was added to the residue and the solvent was again removed in vacuo. This process of adding xylene and then removing solvent in vacuo was repeated twice more, and the petroleum ether (b.p. 60°–80° C.) was added to the residue. The mixture was filtered, and the filtrate concentrated in vacuo to give 6-(7-trimethylsilyloxyheptyl)-7-(3-oxooct-1-enyl)-1,4-dioxaspiro[4,4]-nonane (2.1 g.), $v_{max}$ 845 cm$^{-1}$, 1250 cm$^{-1}$.

(iii) Preparation of 7-(3-hydroxy-3-methyloct-1-enyl)-6-(7-trimethylsilyloxyheptyl)-1,4-dioxaspiro[4,4]nonane A solution (2.86 ml.) of methyl magnesium iodide in diethyl ether [prepared, in the manner well known in the art, from methyl iodide (6 g.), magnesium (1.07 g.) and diethyl ether (20 ml.)] was added dropwise to a stirred solution of 6-(7-trimethylsilyloxyheptyl)-7-(3-oxooct-1-enyl)-1,4-dioxaspiro[4,4]nonane (2.1 g.) in diethyl ether (80 ml.) at room temperature. The mixture was stirred for 30 minutes and a further quantity (1.09 ml.) of the solution of methyl magnesium iodide in diethyl ether was then added dropwise. The mixture was stirred for a further 30 minutes and then added to saturated aqueous ammonium chloride solution (250 ml.) at 0° C. and stirred for 15 minutes. The ether layer was separated and the aqueous layer extracted with diethyl ether. The combined ether layers were concentrated in vacuo to give crude 7-(3-hydroxy-3-methyloct-1-enyl)-6-(7-trimethylsilyloxyheptyl)-1,4-dioxaspiro[4,4]nonane (1.9 g.), $v_{max}$ 845 cm$^{-1}$, 1250 cm$^{-1}$, 3400 cm$^{-1}$, pure enough to use in the next stage.

(iv) Preparation of 6-(7-hydroxyheptyl)-7-(3-hydroxy-3-methyloct-1-enyl)-1,4-dioxaspiro[4,4]nonane Methanol (30 ml.), water (15 ml.) and glacial acetic acid (3 drops) were added to 7-(3-hydroxy-3-methyloct-1-enyl)-6-(7-trimethylsilyloxyheptyl)-1,4-dioxaspiro[4,4]nonane (0.5 g.) and the mixture was stirred at room temperature for 30 minutes. An excess of diethyl ether was then added and the resulting solution was washed with dilute aqueous sodium bicarbonate solution and sodium chloride solution respectively, and dried over sodium sulphate, to give crude 6-(7-hydroxyheptyl)-7-(3-hydroxy-3-methyloct-1-enyl)-1,4-dioxaspiro[4,4]nonane (0.33 g.), $v_{max}$ 3400 cm$^{-1}$, pure enough to use in the next stage.

(v) Preparation of 7-[2-(3-hydroxy-3-methyloct-1-enyl)-5-oxocyclopentyl]heptanol 6-(7-Hydroxyheptyl)-7-(3-hydroxy-3-methyloct-1-enyl)-1,4-dioxaspiro[4,4]nonane (0.33 g.) was hydrolysed by subjecting it to preparative thin layer chromatography on silica gel, eluting with a mixture of hexane, dichloro methane, tetrahydrofuran and glacial acetic acid (30:10:3:3 v/v), to give 7-[2-(3-hydroxy-3-methyloct-1-enyl)-5-oxocyclopentyl]heptanol (0.12 g.), $v_{max}$ 975 cm$^{-1}$, 1720 cm$^{-1}$, 3400 cm$^{-1}$, N.M.R. (approximately 10% solution in deuterochloroform): triplet at 0.9 δ, singlet at 1.30 δ, multiplets at 1.05–2.5 δ, singlet at 1.5 δ, triplet at 3.62 δ(J = 6 cycles/second), multiplet at 5.5–5.7 δ.

Elemental analysis: Found: C, 74.9; H, 11.3%; $C_{21}H_{38}O_3$ requires: C, 74.5; H, 11.3%.

EXAMPLE 4

7-[2-(3-Cyclohexyl-3-oxopropyl)-5-oxocyclopentyl]-heptanol (i) Preparation of 7-(3-cyclohexyl-3-oxoprop-1-enyl)-6-(7-hydroxyheptyl)-1,4-dioxaspiro[4,4]nonane A solution of dimethyl 2-cyclohexyl-2-oxoethylphosphonate (10.1 g.) in dry tetrahydrofuran (40 ml.) was added to a stirred suspension of sodium hydride (1.04 g.) in dry tetrahydrofuran (300 ml.). The mixture was stirred at room temperature until the evolution of hydrogen had ceased, then treated dropwise with a solution of 7-formyl-6-(7-hydroxyheptyl)-1,4-dioxaspiro[4,4]nonane [10.2 g; prepared as described in Example 1(iv) above] in dry tetrahydrofuran (100 ml.) and stirred for a further 2 hours. The mixture was acidified to pH 4 by the addition of glacial acetic acid, the solvents were removed in vacuo, the residue was triturated with diethyl ether and the solid filtered off. The ethereal solution was washed with aqueous sodium carbonate solution, dried over magnesium sulphate, and evaporated to dryness, to give 7-(3-cyclohexyl-3-oxoprop-1-enyl)-6-(7-hydroxyheptyl)-1,4-dioxaspiro[4,4]nonane (16 g.), $v_{max}$ 3400 cm$^{-1}$, 1680 cm$^{-1}$, 1650 cm$^{-1}$, 1620 cm$^{-1}$, 1040 cm$^{-1}$.

The dimethyl 2-cyclohexyl-2-oxoethylphosphonate, used as starting material in the above preparation was prepared by treating a stirred solution of dimethyl methylphosphonate (108 g.) in dry tetrahydrofuran (780 ml.) at −45° to −60° C, under nitrogen, dropwise, during 20 minutes, with a solution of butyl lithium (64 g.) in n-hexane (400 ml.). Stirring was continued at that temperature for a further 10 minutes, and then the mixture was cooled to −60° C. and treated, dropwise during 10 minutes, with a solution of ethyl cyclohexanecarboxylate (68.2 g.) in dry tetrahydrofuran (200 ml.). The mixture was stirred at −60° C. for a further 90 minutes and then at room temperature for 3 hours, and then it was treated with glacial acetic acid (84 ml.), evaporated to dryness in vacuo and the residue treated with water. The mixture was extracted twice with diethyl ether and the combined ethereal extracts were washed with water, dried over sodium sulphate and evaporated to dryness in vacuo. The residue was distilled to give dimethyl 2-cyclohexyl-2-oxoethylphosphonate (52 g.), b.p. 125°–130° C./0.005 mm.Hg, $v_{max}$ 1700 cm$^{-1}$, 1260 cm$^{-1}$, 1040 cm$^{-1}$.

(ii) Preparation of
7-(3-cyclohexyl-3-oxopropyl)-6-(7-hydroxyheptyl)-1,4-dioxaspiro[4,4]nonane A solution of 7-(3-cyclohexyl-3-oxoprop-1-enyl)-6-(7-hydroxyheptyl)-1,4-dioxaspiro[4,4]nonane (2.0 g.) in ethanol (50 ml.) was catalytically reduced with hydrogen at a pressure of 7 kg/cm$^2$ and in the presence of a 5% palladium on charcoal catalyst (0.5 g.) at room temperature for 3 hours. The catalyst was then filtered off and the ethanol evaporated off from the filtrate, to give 7-(3-cyclohexyl-3-oxopropyl)-6-(7-hydroxyheptyl)-1,4-dioxaspiro[4,4]nonane (1.4 g.), $v_{max}$ 3450 cm$^{-1}$, 1700 cm$^{-1}$, 1040 cm$^{-1}$.

(iii) Preparation of
7-[2-(3-cyclohexyl-3-oxopropyl)-5-oxocyclopentyl]heptanol

A mixture of 7-(3-cyclohexyl-3-oxopropyl)-6-(7-hydroxyheptyl)-1,4-dioxaspiro[4,4]nonane (0.5 g.) in hydrochloric acid (20 ml; 1N) was stirred at 60° C. for 2 hours, cooled to ambient temperature and extracted with diethyl ether. The ethereal extract was washed with water, then dried over sodium sulphate. Removal of the solvent under reduced pressure gave a crude product (0.4 g.) which was purified by preparative thin layer chromatography on silica gel, using a mixture of diethyl ether, ethyl acetate and hexane (2:1:1 v/v) as eluant, to give 7-[2-(3-cyclohexyl-3-oxopropyl)-5-oxocyclopentyl]heptan-1-ol (0.16 g.), $v_{max}$ 3450 cm$^{-1}$, 1730 cm$^{-1}$, 1700 cm$^{-1}$, 1060 cm$^{-1}$; Elemental analysis: Found: C, 74.6; H, 10.7%; $C_{21}H_{36}O_3$ requires C, 74.95; H, 10.78%.

EXAMPLE 5

7-[2-(3-Hydroxy-3-methyloct-1-enyl)-5-oxocyclopentyl]heptanol 7-(3-Hydroxy-3-methyloct-1-enyl)-6-(7-trimethylsiloxyheptyl)-1,4-dioxaspiro[4,4]nonane [0.5 g; prepared as hereinbefore described in Example 3(iii)], water (10 ml.) and glacial acetic acid (20 ml.) were left to stand together at room temperature for 6 hours. The solution was then evaporated in vacuo at a temperature below 50° C. Ethyl acetate (150 ml.) was added to the residue and the resulting solution was washed with water until the pH of the washings was 5, dried over sodium sulphate, and evaporated to give a crude product (0.37 g.). The crude product was subjected to preparative thin layer chromatography on silica gel, using a mixture of toluene, dioxan and acetic acid (65:15:1 by volume) as eluant, eluting twice, to give 7-[2-(3-hydroxy-3-methyloct-1-enyl)-5-oxocyclopentyl]heptanol (0.12 g.).

Elemental analysis: Found: C, 72.9; H, 11.2%; $C_{21}H_{38}O_3 \cdot \frac{1}{2}H_2O$ requires C, 72.6; H, 11.3%

EXAMPLE 6

7-[2-(3-Hydroxy-3-methylhex-1-enyl)-5-oxocyclopentyl]heptanol (i) Preparation of
6-(7-hydroxyheptyl)-7-(3-oxohex-1-enyl)-1,4-dioxaspiro[4,4]nonane By proceeding in a similar manner to that described in Example 3(i) for the preparation of 6-(7-hydroxyheptyl)-7-(3-oxooct-1-enyl)-1,4-dioxaspiro[4,4]nonane, but substituting the appropriate quantity of butyrylmethylenetriphenylphosphorane for the hexanoylmethylenetriphenylphosphorane used as a starting material, there was prepared 6-(7-hydroxyheptyl)-7-(3-oxohex-1-enyl)-1,4-dioxaspiro[4,4]nonane, $v_{max}$ 1620 cm$^{-1}$, 1660 cm$^{-1}$.

The butyrylmethylenetriphenylphosphorane (m.p. 158°–161° C.), used as a starting material in the above preparation, was prepared from 1-chloropentan-2-one, via 2-oxopentyltriphenylphosphonium chloride (m.p. 159° C.), by proceeding in a similar manner to that hereinbefore described in Example 3(i) for the preparation of hexanoylmethylenetriphenylphosphorane from 1-chloroheptan-2-one.

(ii) Preparation of
6-(7-trimethylsiloxyheptyl)-7-(3-oxohex-1-enyl)-1,4-dioxaspiro[4,4]nonane By proceeding in a similar manner to that hereinbefore described in Example 3(ii) for the preparation of 6-(7-trimethylsiloxyheptyl)-7-(3-oxooct-1-enyl)-1,4-dioxaspiro[4,4]nonane, but substituting the appropriate quantity of 6-(7-hydroxyheptyl)-7-(3-oxohex-1-enyl)-1,4-dioxaspiro[4,4]nonane for the 6-(7-hydroxy-heptyl)-7-(3-oxooct-1-enyl)-1,4-dioxaspiro[4,4]nonane used as starting material, there was prepared 6-(7-trimethylsiloxyheptyl)-7-(3-oxohex-1-enyl)-1,4-dioxaspiro[4,4]-nonane, $v_{max}$ 845 cm$^{-1}$, 1250 cm$^{-1}$.

(iii) Preparation of
7-(3-hydroxy-3-methylhex-1-enyl)-6-(7-trimethylsiloxyheptyl)-1,4-dioxaspiro[4,4]nonane By proceeding in a similar manner to that hereinbefore described in Example 3(iii) for the preparation of 7-(3-hydroxy-3-methyloct-1-enyl)-6-(7-trimethylsiloxyheptyl)-1,4-dioxaspiro[4,4]nonane, but substituting the appropriate quantity of 6-(7-trimethylsiloxyheptyl)-7-(3-oxohex-1-enyl)-1,4-dioxaspiro[4,4]nonane for the 6-(7-trimethylsiloxyheptyl)-7-(3-oxooct-1-enyl)-1,4-dioxaspiro[4,4]nonane used as starting material, there was prepared 7-(3-hydroxy-3-methylhex-1-enyl)-6-(7-trimethylsiloxyheptyl)-1,4-dioxaspiro[4,4]nonane, $v_{max}$ 845 cm$^{-1}$, 1250 cm$^{-1}$, 3400 cm$^{-1}$.

(iv) Preparation of
7-[2-(3-hydroxy-3-methylhex-1-enyl)-5-oxocyclopentyl]heptanol By proceeding in a similar manner to that hereinbefore described in Example 5 for the preparation of 7-[2-(3-hydroxy-3-methyloct-1-enyl)-5-oxocyclopentyl]heptanol, but substituting the appropriate quantity of 7-(3-hydroxy-3-methylhex-1-enyl)-6-(7-trimethylsiloxyheptyl)-1,4-dioxaspiro[4,4]nonane for the 7-(3-hydroxy-3-methyloct-1-enyl)-6-(7-trimethylsiloxyheptyl)-1,4-dioxaspiro[4,4]nonane used as starting material, there was prepared 7-[2-(3-hydroxy-3-methylhex-1-enyl)-5-oxocyclopentyl]heptanol. Elemental analysis: Found: C, 73.3; H, 10.9%; $C_{19}H_{34}O_3$ requires C, 73.5; H, 11.0%. N.M.R. (approximately 10% w/v solution in deuterochloroform): triplet at 0.9δ, singlet at 1.3δ, multiplets at 1.05–2.5δ, singlet at 1.75δ, triplet at 3.62δ, multiplet at 5.5–5.7δ.

EXAMPLE 7

7-[2-(5-Ethoxy-3-hydroxy-3-methylpent-1-enyl)-5-oxocyclopentyl]heptanol (i) Preparation of 6-(7-hydroxyheptyl)-7-(5-ethoxy-3-oxopent-1-enyl)-1,4-dioxaspiro[4,4]nonane By proceeding in a similar manner to that hereinbefore described in Example 3(i) for the preparation of 6-(7-hydroxyheptyl)-7-(3-oxooct-1-enyl)-1,4-dioxaspiro[4,4]nonane, but substituting the appropriate quantity of 3-ethoxypropionylmethylenetriphenylphosphorane for the hexanoylmethylenetriphenylphosphorane used as a starting material, there was prepared 6-(7-hydroxyheptyl)-7-(5-ethoxy-3-oxopent-1-enyl)-1,4-dioxaspiro[4,4]nonane, $\nu_{max}$ 1620 cm$^{-1}$, 1660 cm$^{-1}$.

The 3-ethoxypropionylmethylenetriphenylphosphorane (m.p. 63°–65° C.), used as a starting material in the above preparation, was prepared from 1-chloro-4-ethoxybutan-2-one, via 4-ethoxy-2-oxobutyltriphenylphosphonium chloride (m.p. 157°–160° C.), by proceeding in a similar manner to that hereinbefore described in Example 3(i) for the preparation of hexanoylmethylenetriphenylphosphorane from 1-chloroheptan-2-one.

(ii) Preparation of 6-(7-trimethylsiloxyheptyl)-7-(5-ethoxy-3-oxopent-1-enyl)-1,4-dioxaspiro[4,4]nonane By proceeding in a similar manner to that hereinbefore described in Example 3(ii) for the preparation of 6-(7-trimethylsiloxyheptyl)-7-(3-oxooct-1-enyl)-1,4-dioxaspiro[4,4]nonane, but substituting the appropriate quantity of 6-(7-hydroxyheptyl)-7-(5-ethoxy-3-oxopent-1-enyl)-1,4-dioxaspiro[4,4]nonane for the 6-(7-hydroxyheptyl)-7-(3-oxooct-1-enyl)-1,4-dioxaspiro[4,4]nonane used as starting material, there was prepared 6-(7-trimethylsiloxyheptyl)-7-(5-ethoxy-3-oxopent-1-enyl)-1,4-dioxaspiro[4,4]nonane, $\nu_{max}$ 845 cm$^{-1}$, 1250 cm$^{-1}$.

(iii) Preparation of 7-(5-ethoxy-3-hydroxy-3-methylpent-1-enyl)-6-(7-trimethylsiloxyheptyl)-1,4-dioxaspiro[4,4]nonane By proceeding in a similar manner to that hereinbefore described in Example 3(iii) for the preparation of 7-(3-hydroxy-3-methyloct-1-enyl)-6-(7-trimethylsiloxyheptyl)-1,4-dioxaspiro[4,4]nonane, but substituting the appropriate quantity of 6-(7-trimethylsiloxyheptyl)-7-(5-ethoxy-3-oxopent-1-enyl)-1,4-dioxaspiro[4,4]nonane for the 6-(7-trimethylsiloxyheptyl)-7-(3-oxooct-1-enyl)-1,4-dioxaspiro[4,4]nonane used as starting material, there was prepared 7-(5-ethoxy-3-hydroxy-3-methylpent-1-enyl)-6-(7-trimethylsiloxyheptyl)-1,4-dioxaspiro[4,4]nonane, $\nu_{max}$ 845 cm$^{-1}$, 1250 cm$^{-1}$, 3450 cm$^{-1}$.

(iv) Preparation of 7-[2-(5-ethoxy-3-hydroxy-3-methylpent-1-enyl)-5-oxocyclopentyl]heptanol By proceeding in a similar manner to that hereinbefore described in Example 5 for the preparation of 7-[2-(3-hydroxy-3-methyloct-1-enyl)-5-oxocyclopentyl]heptanol, for substituting the appropriate quantity of 7-(5-ethoxy-3-hydroxy-3-methylpent-1-enyl)-6-(7-trimethylsiloxyheptyl)-1,4-dioxaspiro[4,4]nonane for the 7-(3-hydroxy-3-methyloct-1-enyl)-6-(7-trimethylsiloxyheptyl)-1,4-dioxaspiro[4,4]nonane used as starting material, there was prepared 7-[2-(5-ethoxy-3-hydroxy-3-methylpent-1-enyl)-5-oxocyclopentyl]heptanol. Elemental analysis: Found: C, 69.2; H, 10.9%; $C_{20}H_{36}O_4 \cdot 1/2H_2O$ requires C, 68.9; H, 10.4% $\nu_{max}$ 975 cm$^{-1}$, 1720 cm$^{-1}$, 3400 cm$^{-1}$. N.M.R. (approximately 10% w/v solution in deuterochloroform): triplet at 1.18$\delta$ (J = 7 cycles/second), singlet at 1.3$\delta$, multiplets at 1.0–2.8$\delta$, 3.3–3.8$\delta$, 5.6–5.7$\delta$.

EXAMPLE 8

2-(7-Acetoxyheptyl)-3-(5-ethoxy-3-hydroxy-3-methylpent-1-enyl)cyclopentanone

A solution of 7-[2-(5-ethoxy-3-hydroxy-3-methylpent-1-enyl)-5-oxocyclopentyl]heptanol [0.4 g; prepared as hereinbefore described in Example 7(iv)] in dry pyridine (4 ml.) was treated with acetic anhydride (4 ml.) and the resulting solution was allowed to stand at ambient temperature for 3 days and then diluted with water (100 ml.) with external cooling by means of an ice-bath. The resulting aqueous solution was extracted three times with chloroform, and the combined extracts were dried over sodium sulphate. Evaporation in vacuo gave a crude product which was purified by preparative thin layer chromatography on silica gel using a mixture of toluene, dioxan and acetic acid (65:15:1 by volume) as eluant, to give 2-(7-acetoxyheptyl)-3-(5-ethoxy-3-hydroxy-3-methylpent-1-enyl)cyclopentanone (0.17 g.). Elemental analysis: Found: C, 68.7; H, 10.3%; $C_{22}H_{38}O_5$ requires C, 69.1; H, 10.0%. N.M.R. (approximately 10% w/v solution in deuterochloroform): multiplets at 1.0–1.9$\delta$, 1.9–2.9$\delta$, singlet at 2.05$\delta$, multiplet at 3.35$\delta$, triplet at 4.05$\delta$, (J = 6.5 cycles/second), multiplet at 5.6$\delta$.

EXAMPLE 9

7-[5-(3-Oxo-ω-phenylalk-1-enyl)-2-oxocyclopentyl]heptanols (i) Preparation of 7-[5-(3-oxo-ω-phenylalk-1-enyl)-2-oxocyclopentyl]heptanols A suspension of 6-(7-hydroxyheptyl)-7-(3-phenyl-3-oxoprop-1-enyl)-1,4-dioxaspiro[4,4]nonane [1.0 g; prepared as hereinafter described in Example 9(ii)] at dilute hydrochloric acid (2N; 30 ml.) was stirred in 60°–65° C. for 1 hour. The mixture was extracted with diethyl ether and then the combined ethereal extracts were washed with aqueous sodium bicarbonate solution (10% w/v) and then with water, and then dried over anhydrous magnesium sulphate. The solution was evaporated and the residue was purified by preparative thin layer chromatography on silica gel, using a mixture of diethyl ether, n-hexane and ethyl acetate (2:1:1 by volume) as eluant, to give 7-[5-(3-oxo-3-phenylprop-1-enyl)-2-oxocyclopentyl]heptanol (0.16 g.), in the form of a yellow oil. [Elemental analysis: Found: C, 76.9; H, 8.9%; $C_{21}H_{28}O_3$ requires C, 76.8; H, 8.6%, $\nu_{max}$ 990 cm$^{-1}$, 1620 cm$^{-1}$, 1665 cm$^{-1}$, 3400 cm$^{-1}$. N.M.R. (approximately 10% w/v solution in deuterochloroform): triplet at 3.6$\delta$ (J = 6 cycles/second), multiplets at 7.85–8.05$\delta$, 7.4–7.65$\delta$, 6.85–7.15$\delta$, 2–2.9$\delta$ and 1.1–2.0$\delta$].

By proceeding in a similar manner, but replacing the 6-(7-hydroxyheptyl)-7-(3-phenyl-3-oxoprop-1-enyl)-1,4-dioxaspiro[4,4]nonane used as starting material by the appropriate quantities of 6-(7-hydroxyheptyl)-7-(3-oxo-6-phenylhex-1-enyl)-1,4-dioxaspiro[4,4]nonane, 6-(7-hydroxyheptyl)-7-(3-oxo-5-phenylpent-1-enyl)-1,4-dioxaspiro[4,4]nonane and 6-(7-hydroxyheptyl)-7-(3-oxo-4-phenylbut-1-enyl)-1,4-dioxaspiro[4,4]nonane [all three prepared as hereinafter described in Example 9(ii)], there were prepared 7-[5-(3-oxo-6-phenylhex-1-enyl)-2-oxocyclopentyl]heptanol [Elemental analysis: Found: C, 77.9; H, 9.4%; $C_{24}H_{34}O_3$ requires C, 77.8; H, 9.25%. $\nu_{max}$ 990 cm$^{-1}$, 1625 cm$^{-1}$, 1665 cm$^{-1}$, 1685 cm$^{-1}$, 1725 cm$^{-1}$, 3400 cm$^{-1}$].

N.M.R. (approximately 10% w/v solution in deuterochloroform): singlets at 7.26δ and 1.79δ, doublet at 6.16δ (J = 16 cycles/second), doublet of doublets at 6.7δ (J = 16 and 7.5 cycles/second), triplet at 3.61δ (J = 6 cycles/second), multiplets at 1.95–2.9δ and 1.1–1.95δ], 7-[5-(3-oxo-5-phenylpent-1-enyl)-2-oxocyclopentyl]heptanol [Elemental analysis: Found: C, 77.6; H, 9.2%; $C_{23}H_{32}O_3$ requires C, 77.5; H, 9.05%. $\nu_{max}$ 985 cm$^{-1}$, 1625 cm$^{-1}$, 1660 cm$^{-1}$, 1685 cm$^{-1}$, 1730 cm$^{-1}$, 3450 cm$^{-1}$. N.M.R. (approximately 10% w/v solution in deuterochloroform): singlet at 1.98δ, doublet at 6.16δ (J = 15.5 cycles/second), doublet of doublets at 6.77δ (J = 15.5 and 7.5 cycles/second), triplet at 3.61δ (J = 6 cycles/second), multiplets at 7.25δ, 2.93δ and 1.0–2.8δ], and 7-[5-(3-oxo-4-phenylbut-1-enyl)-2-oxocyclopentyl]heptanol [Elemental analysis: Found: C, 76.9; H, 9.2%; $C_{22}H_{30}O_3$ requires C, 77.15; H, 8.8%. $\nu_{max}$ 990 cm$^{-1}$, 1625 cm$^{-1}$, 1670 cm$^{-1}$, 1690 cm$^{-1}$, 1730 cm$^{-1}$, 3450 cm$^{-1}$; N.M.R. (approximately 10% w/v solution in deuterochloroform): singlet at 3.82δ, doublet at 6.20δ, (J = 15.5 cycles/second), doublet of doublets at 6.85δ (J = 15.5 and 7.5 cycles/second), triplet at 3.6δ (J = 6 cycles/second), multiplets at 7.28δ and 1.0–2.9δ], respectively.

(ii) Preparation of 6-(7-hydroxyheptyl)-7-(3-oxo-ω-phenylalk-1-enyl)-1,4-dioxaspiro[4,4]nonanes (a) A mixture of 7-formyl-6-(7-hydroxyheptyl)-1,4-dioxaspiro[4,4]nonane [4.0 g; prepared as hereinbefore described in Example 1(iv)] and benzoylmethylenetriphenylphosphorane (5.6 g; prepared according to the method of F. Ramirez and S. Dershowitz, J. Org. Chem. 1957, 22, 41) in hexamethylphosphotriamide (35 ml.) was heated on a steam bath under dry nitrogen for 48 hours then poured into water (200 ml.). The mixture was extracted with diethyl ether and the ethereal solution was washed with water, dried over anhydrous magnesium sulphate and evaporated. The residue was triturated with a mixture of petroleum ether (b.p. 40°–60° C.) and diethyl ether, allowed to stand at 0° C, then filtered to remove triphenylphosphine oxide. The filtrate was evaporated to give 6-(7-hydroxyheptyl)-7-(3-phenyl-3-oxoprop-1-enyl)-1,4-dioxaspiro[4,4]nonane (5.5 g.) ($\nu_{max}$ 950 cm$^{-1}$, 985 cm$^{-1}$, 1615 cm$^{-1}$, 1660 cm$^{-1}$, 3380 cm$^{-1}$).

By proceeding in a similar manner, but substituting the appropriate quantity of 4-phenylbutanoylmethylenetriphenylphosphorane [prepared as hereinafter described in Example 9(iii)] for the benzoylmethylenetriphenylphosphorane used as a starting material, there was prepared 6-(7-hydroxyheptyl)-7-(3-oxo-6-phenylhex-1-enyl)-1,4-dioxaspiro[4,4]nonane ($\nu_{max}$ 950 cm$^{-1}$, 990 cm$^{-1}$, 1620 cm$^{-1}$, 1680 cm$^{-1}$, 3335 cm$^{-1}$).

(b) A solution of dimethyl 2-oxo-4-phenylbutylphosphonate [2.5g; prepared as described hereinafter in Example 9(iv)] in anhydrous tetrahydrofuran (50 ml.) was added to a stirred suspension of sodium hydride (0.24 g.) in tetrahydrofuran (20 ml.). The mixture was stirred at room temperature in an atmosphere of nitrogen for 24 hours, then treated dropwise with a solution of 7-formyl-6-(7-hydroxyheptyl)-1,4-dioxaspiro[4,4]nonane [2.7 g; prepared as described hereinbefore in Example 1(iv)] in tetrahydrofuran (30 ml.) and stirred for a further 2 hours in an atmosphere of nitrogen. The mixture was acidified to pH 4 by the addition of glacial acetic acid, the solvents were removed in vacuo and the residue was extracted with diethyl ether. The ethereal solution was washed with aqueous sodium bicarbonate solution (10% w/v) and then with water and dried over anhydrous magnesium sulphate. Evaporation of the solution gave 6-(7-hydroxyheptyl)-7-(3-oxo-5-phenylpent-1-enyl)-1,4-dioxaspiro[4,4]nonane (3.9 g.), in the form of a yellow oil ($\nu_{max}$ 955 cm$^{-1}$, 990 cm$^{-1}$, 1625 cm$^{-1}$, 1665 cm$^{-1}$, 1690 cm$^{-1}$).

By proceeding in a similar manner, but substituting the appropriate quantity of dimethyl 2-oxo-3-phenylpropylphosphonate [prepared as hereinafter described in Example 9(iv)] for the dimethyl 2-oxo-4-phenylbutylphosphonate used as a starting material, there was prepared 6-(7-hydroxyheptyl)-7-(3-oxo-4-phenylbut-1-enyl)-1,4-dioxaspiro[4,4]nonane ($\nu_{max}$ 955 cm$^{-1}$, 990 cm$^{-1}$, 1625 cm$^{-1}$, 1665 cm$^{-1}$, 1685 cm$^{-1}$).

(iii) Preparation of 4-phenylbutanoylmethylenetriphenylphosphorane

4-Phenylbutanoyl chloride (14.7 g.) was added dropwise to a stirred solution of diazomethane (7.5 g.) in diethyl ether (340 ml.) at 0° C. The solution was stirred in an ice bath for 1 hour further and then it was saturated with anhydrous hydrogen chloride gas. After 1 hour at 0° C, dry nitrogen was passed through this solution, which was then poured onto crushed ice (about 300 ml.). The ethereal layer was separated and the aqueous phase was diluted with water (150 ml.), saturated with sodium chloride, and extracted with diethyl ether. The combined ethereal solutions were washed with water, aqueous sodium carbonate solution (2N), and then again with water, and dried over anhydrous magnesium sulphate. The solution was evaporated and the residue was distilled, to give 1-chloro-2-oxo-5-phenylpentane (11.5 g.), b.p. 150°–151° C./10 mm.Hg (Elemental analysis: C, 67.4; H, 7.1; Cl, 18.0%; $C_{11}H_{13}ClO$ requires C, 67.2; H, 6.7; Cl, 18.0%. $\nu_{max}$ 1455 cm$^{-1}$, 1500 cm$^{-1}$, 1725 cm$^{-1}$).

A solution of 1-chloro-2-oxo-5-phenylpentane (6.55 g.) in dry chloroform (30 ml.) was added to a solution of triphenylphosphine (8.7 g.) in dry chloroform (30 ml.) and heated at reflux in an atmosphere of dry nitrogen for 4 hours. The solution was then evaporated under reduced pressure and the residual oil was triturated with a mixture of light petroleum ether (b.p. 40°–60° C.) and diethyl ether, to give a white solid. Recrystallisation of this material from a mixture of dichloromethane and diethyl ether gave 4-phenylbutanoylmethyltriphenylphosphonium chloride (11.2 g.) in the form of a white crystalline solid. m.p. 192–195° C. (Elemental analysis: C, 76.0; H, 6.2%; $C_{29}H_{28}ClOP$ requires: C, 75.9; H, 6.2%; $\nu_{max}$ 1110 cm$^{-1}$, 1445 cm$^{-1}$, 1490 cm$^{-1}$, 1695 cm$^{-1}$).

A solution of sodium (0.1 g.) in anhydrous ethanol (3.8 ml.) was added to a solution of 4-phenylbutanoylmethyltriphenylphosphonium chloride (1.0 g.) in anhydrous ethanol (10 ml.) and the resulting mixture was left to stand at room temperature for 4 hours. The mixture was concentrated to half its bulk by removal of ethanol in vacuo and then diluted with water (50 ml.) and extracted with chloroform. The combined chloroform extracted were washed with water, dried over sodium sulphate and evaporated to dryness. The residual oil was triturated with light petroleum ether (b.p. 40°–60°

C.) and then recrystallised from cyclohexane, to give 4-phenylbutanoylmethylenetriphenylphosphorane (0.6 g.), in the form of a white crystalline solid, m.p. 93°-95° C, (Elemental analysis: C, 82.8; H, 6.5; P, 7.6%; $C_{29}H_{27}OP$ requires: C, 82,4; H, 6.4; P, 7.3%; $\nu_{max}$ 1100 cm$^{-1}$, 1400 cm$^{-1}$, 1440 cm$^{-1}$, 1485 cm$^{-1}$, 1540 cm$^{-1}$).

(iv) Preparation of dimethyl 2-oxo-ω-phenylalkylphosphonates

A solution of butyl lithium (9.6 g.) in hexane (97 ml.) and anhydrous diethyl ether (160 ml.) was added during 20 minutes to a stirred solution of dimethyl methylphosphonate (18.6 g.) in anhydrous tetrahydrofuran (80 ml.) at −50° C, in an atmosphere of nitrogen. The solution was stirred for a further 15 minutes at −60° C, and then a solution of ethyl β-phenylpropionate (13.4 g.) in anhydrous tetrahydrofuran (60 ml.) was added during 10 minutes at −60° C. This solution was stirred at −60° C, for 90 minutes and then at the ambient temperature for 150 minutes. Glacial acetic acid (14.2 ml.) was then added and the solvents were evaporated off. Water (75 ml.) was added to the gelatinous residue and then the mixture was extracted with diethyl ether. The ethereal extracts were washed with water, dried over anhydrous magnesium sulphate and the ether was then removed in vacuo.

The residue was distilled, to give dimethyl 2-oxo-4-phenylbutylphosphonate (10.7 g.) in the form of a colourless oil, b.p. 155°-158° C./0.1 mm.Hg. (Elemental analysis: C, 56.4; H, 6.9; P, 11.8%; $C_{12}H_{17}O_4P$ requires: C, 56.25; H, 6.7; P, 12.1%; $\nu_{max}$ 835 cm$^{-1}$, 1035 cm$^{-1}$, 1180 cm$^{-1}$, 1260 cm$^{-1}$, 1455 cm$^{-1}$, 1710 cm$^{-1}$).

By proceeding in a similar manner, but replacing the ethyl β-phenylpropionate used as a starting material by the appropriate quantity of ethyl phenylacetate, there was prepared dimethyl 2-oxo-3-phenylpropylphosphonate (b.p. 143°-150° C./0.1 mm.Hg; Elemental analysis: C, 54.6; H, 6.3%; $C_{11}H_{15}O_4P$ requires: C, 54.5; H, 6.2%; $\nu_{max}$ 835 cm$^{-1}$, 1035 cm$^{-1}$, 1180 cm$^{-1}$, 1260 cm$^{-1}$, 1455 cm$^{-1}$, 1710 cm$^{-1}$).

EXAMPLE 10

7-{5-[3-Oxo-4-(2-phenylethyl)oct-1-enyl]-2-oxocyclopentyl}heptanol (i) Preparation of 7-{5-[3-oxo-4-(2-phenylethyl)oct-1-enyl]-2-oxocyclopentyl}heptanol A solution of 6-(7-hydroxyheptyl)-7-[3-oxo-4-(2-phenylethyl)oct-1-enyl]-1,4-dioxospiro[4,4]nonane [0.5 g; prepared as hereinafter described in Example 10(ii)] in acetic acid (12 ml.) and water (6 ml.) was kept at room temperature for 4 hours then evaporated in vacuo at a temperature below 50° C. The residue was dissolved in diethyl ether and the ethereal solution was washed with water, dried over magnesium sulphate and evaporated. The residue was subjected to preparative thin layer chromatography on silica gel, using a mixture of diethyl ether, n-hexane and ethyl acetate (2:1:1 by volume) as eluant, to give 7-{5-[3-oxo-4-(2-phenylethyl)oct-1-enyl]-2-oxocyclopentyl}heptanol (0.11 g.) in the form of a yellow oil [Elemental analysis: Found: C, 78.9; H, 10.2%; $C_{28}H_{42}O_3$ requires C, 78.8; H, 9.9%; $\nu_{max}$ 990 cm$^{-1}$, 1620 cm$^{-1}$, 1655 cm$^{-1}$, 1680 cm$^{-1}$, 1725 cm$^{-1}$, 3400 cm$^{-1}$, N.M.R. (approximately 10% w/v solution in deuterochloroform): singlet at 7.21δ, doublet at 6.20δ (J = 16.5 cycles/second), doublet of doublets at 6.76δ (J = 7.5 and 16.5 cycles/second), triplets at 3.6δ (J = 6 cycles/second) and 0.86δ, multiplets at 2.1-2.8δ, 1.05-2.1δ].

(ii) Preparation of 6-(7-hydroxyheptyl)-7-[4-(2-phenylethyl)-3-oxooct-1-enyl]-1,4-dioxaspiro[4,4]nonane By proceeding in a similar manner to that hereinbefore described in Example 9(ii)(b), but replacing the dimethyl 2-oxo-4-phenylbutylphosphonate used as starting material by the appropriate quantity of dimethyl 2-oxo-3-(2-phenylethyl)heptylphosphonate [prepared as hereinafter described in Example 10(iii)], there was prepared 6-(7-hydroxyheptyl)-7-[4-(2-phenylethyl)-3-oxooct-1-enyl]-1,4-dioxaspiro[4,4]nonane ($\nu_{max}$ 950 cm$^{-1}$, 990 cm$^{-1}$, 1620 cm$^{-1}$, 1655 cm$^{-1}$, 1680cm$^{-1}$).

(iii) Preparation of dimethyl 2-oxo-3-(2-phenylethyl)-heptylphosphonate

By proceeding in a similar manner to that hereinbefore described in Example 9(iv), but replacing the ethyl β-phenylpropionate used as a starting material by the appropriate quantity of ethyl 2-(2-phenylethyl-hexanoate, there was prepared dimethyl 2-oxo-3-(2-phenylethyl)heptylphosphonate (b.p. 162°-172° C./0.15 mm.Hg; Elemental analysis: C, 62.6; H, 8.6; P, 9.3%, $C_{17}H_{27}O_4P$ requires: C, 62.6; H, 8.3; P, 9.5% $\nu_{max}$ 810 cm$^{-1}$, 1030 cm$^{-1}$, 1180 cm$^{-1}$, 1260 cm$^{-1}$, 1455 cm$^{-1}$, 1700 cm$^{-1}$).

The ethyl 2-(2-phenylethyl)hexanoate, used as a starting material, was prepared by heating at reflux for 18 hours a solution of 2-(2-phenylethyl)hexanoic acid (17.0 g.) in anhydrous ethanol (15.5 ml) and concentrated sulphuric acid (1.5 ml.). The solution was then added to water (150 ml.) and the oil which separated was extracted with diethyl ether. The ethereal solution was washed successively with water, aqueous sodium carbonate solution (2N), and water, and then dried over anhydrous magnesium sulphate and evaporated. The residue was distilled, to give ethyl 2-(2-phenylethyl)-hexanoate (15.25 g.) in the form of a colourless oil, b.p. 158°-160° C./7 mm.Hg (Elemental analysis: C, 77.5; H, 9.9%; $C_{16}H_{24}O_2$ requires: C, 77.4; H, 9.7%).

EXAMPLE 11

7-[2-(4-Methyl-3-oxopent-1-enyl)-5-oxocyclopentyl]-heptanol (i) Preparation of 6-(7-hydroxyheptyl)-7-(4-methyl-3-oxopent-1-enyl)-1,4-dioxaspiro[4,4]nonane By proceeding in a similar manner to that hereinbefore described in Example 1(v), but substituting the appropriate quantity of dimethyl 3-methyl-2-oxobutylphosphonate for the dimethyl 3-methyl-2-oxoheptylphosphonate used as a starting material, there was prepared 6-(7-hydroxyheptyl)-7-(4-methyl-3-oxopent-1-enyl)-1,4-dioxaspiro[4,4]nonane, $\nu_{max}$ 3400 cm$^{-1}$, 1680 cm$^{-1}$, 1655 cm$^{-1}$, 1615 cm$^{-1}$, 1385 cm$^{-1}$, 1040 cm$^{-1}$.

The dimethyl 3-methyl-2-oxobutylphosphonate (b.p. 125°-135° C./11 mm.Hg; $\nu_{max}$ 2950 cm$^{-1}$, 1710 cm$^{-1}$, 1470 cm$^{-1}$, 1260 cm$^{-1}$, 820 cm$^{-1}$), used as a starting material in the above preparation, was prepared by proceeding in a similar manner to that hereinbefore described in Example 9(iv) for the preparation of dimethyl 2-oxo-4-phenylbutylphosphonate, but substituting the appropriate quantity of ethyl isobutyrate for the ethyl β-phenylpropionate used as starting material.

(ii) Preparation of 7-[2-(4-methyl-3-oxopent-1-enyl)-5-oxocyclopentyl]heptanol By proceeding in a similar manner to that hereinbefore described in Example 1(vi), but substituting the appropriate quantity of 6-(7-hydroxyheptyl)-7-(4-methyl-3-oxopent-1-enyl)-1,4-dioxaspiro[4,4]nonane for the 6-(7-hydroxyheptyl)-7-(4-methyl-3-oxooct-1-enyl)-1,4-dioxaspiro[4,4]nonane used as starting material, there was prepared 7-[2-(4-methyl-3-oxopent-1-enyl)-5-oxocyclopentyl]heptanol. Elemental analysis: Found: C, 73.9; H, 10.8%; $C_{18}H_{30}O_3$ requires C, 73.4; H, 10.3%; $\nu_{max}$ 3450 cm$^{-1}$, 1730 cm$^{-1}$, 1690 cm$^{-1}$, 1660 cm$^{-1}$, 1620 cm$^{-1}$, 1385 cm$^{-1}$, 990 cm$^{-1}$; N.M.R. (approximately 10% w/v solution in deuterochloroform): septuplet at 2.88$\delta$, multiplets at 1.8–2.8$\delta$ and 1.2–1.8$\delta$, doublet of doublets at 6.9$\delta$ (J = 7.5 and 15.5 cycles/second), triplet at 3.65$\delta$ (J = 6 cycles/second), doublets at 6.27$\delta$ (J = 15.5 cycles/second) and 1.17$\delta$ (J = 7 cycles/second) and singlet at 2.1$\delta$.

EXAMPLE 12

7-[2-(3-Hydroxy-4-phenoxybut-1-enyl)-5-oxocyclopentyl]heptanol

(i) Preparation of 6-(7-hydroxyheptyl)-7-(3-oxo-4-phenoxybut-1-enyl)-1,4-dioxaspiro[4,4]nonane By proceeding in a similar manner to that hereinbefore described in Example 9(ii), but replacing the benzoylmethylenetriphenylphosphorane used as a starting material by the appropriate quantity of phenoxyacetylmethylenetriphenylphosphorane, there was prepared 6-(7-hydroxyheptyl)-7-(3-oxo-4-phenoxybut-1-enyl)-1,4-dioxaspiro[4,4]nonane.

The phenoxyacetylmethylenetriphenylphosphorane, used as a starting material, was prepared as follows:

A solution of 1-chloro-3-phenoxyacetone (6.8 g.) and triphenylphosphine (12 g.) in chloroform (16 ml.) was saturated with nitrogen and heated at reflux under nitrogen overnight. An excess of dry diethyl ether was added, and then the solvents were decanted from the gum that separated. The remaining solvent was removed in vacuo to give crude 2-oxo-3-phenoxypropyltriphenylphosphonium chloride (10.35 g.). This was stirred vigorously with a solution of sodium carbonate (18 g.) in water (180 ml.) for 24 hours. The solution was extracted with diethyl ether and the ethereal extracts dried over sodium sulphate. The solvent was removed by evaporation to give phenoxyacetylmethylenetriphenylphosphorane (5.3 g.), a sticky solid.

The 1-chloro-3-phenoxyacetone, used as a starting material, was prepared as follows:

8N Jones reagent (100 ml.) was added dropwise to a stirred solution of 1-chloro-2-hydroxy-3-phenoxypropane (28.3 g.) in acetone (100 ml.) during 1 hour while maintaining the reaction temperature at 20° C. The mixture was then stirred for 4 hours, and then sufficient water was added to dissolve the precipitated chromium salts. The mixture was extracted three times with diethyl ether and the combined ethereal extracts were dried over sodium sulphate, concentrated under reduced pressure, dried again over sodium sulphate, and concentrated further and distilled, to give 1-chloro-3-phenoxyacetone (13.9 g.), b.p. 150°–155° C./20 mm.Hg.

(ii) Preparation of 6-(7-hydroxyheptyl)-7-(3-hydroxy-4-phenoxybut-1-enyl)-1,4-dioxaspiro[4,4]nonane By proceeding in a similar manner to that hereinbefore described in Example 2(i), but replacing the 6-(7-hydroxyheptyl)-7-(4-methyl-3-oxooct-1-enyl)-1,4-dioxaspiro[4,4]nonane used as starting material by the appropriate quantity of 6-(7-hydroxyheptyl)-7-(3-oxo-4-phenoxybut-1-enyl)-1,4-dioxaspiro[4,4]nonane, there was prepared 6-(7-hydroxyheptyl)-7-(3-hydroxy-4-phenoxybut-1-enyl)-1,4-dioxaspiro[4,4]nonane.

(iii) Preparation of 7-[2-(3-hydroxy-4-phenoxybut-1-enyl)-5-oxocyclopentyl]heptanol By proceeding in a similar manner to that hereinbefore described in Example 2(ii), but replacing the 6-(7-hydroxyheptyl)-7-(3-hydroxy-4-methyloct-1-enyl)-1,4-dioxaspiro[4,4]nonane used as starting material by the appropriate quantity of 6-(7-hydroxyheptyl)-7-(3-hydroxy-4-phenoxybut-1-enyl)-1,4-dioxaspiro[4,4]nonane, there was prepared 7-[2-(3-hydroxy-4-phenoxybut-1-enyl)-5-oxocyclopentyl]heptanol [Elemental analysis: Found: C, 72.9; H, 9.0%; $C_{22}H_{32}O_4$ requires C, 73.2; H, 9.0%; $\nu_{max}$ 3400 cm$^{-1}$, 1720 cm$^{-1}$, 975 cm$^{-1}$; N.M.R. (approximately 10% w/v solution in deuterochloroform): multiplets at 1.0–2.8$\delta$, 3.5–4.1$\delta$, 4.3–4.7$\delta$, 5.6–5.9$\delta$, 6.8–7.5$\delta$].

EXAMPLE 13

7-[2-(3-Hydroxy-3-methyl-4-phenoxybut-1-enyl)-5-oxocyclopentyl]heptanol

(i) Preparation of 6-(7-trimethylsiloxyheptyl)-7-(3-oxo-4-phenoxybut-1-enyl)-1,4-dioxaspiro[4,4]nonane By proceeding in a similar manner to that hereinbefore described in Example 3(ii), but replacing the 6-(7-hydroxyheptyl)-7-(3-oxooct-1-enyl)-1,4-dioxaspiro[4,4]nonane by the appropriate quantity of 6-(7-hydroxyheptyl)-7-(3-oxo-4-phenoxybut-1-enyl)-1,4-dioxaspiro[4,4]nonane, there was prepared 6-(7-trimethylsiloxyheptyl)-7-(3-oxo-4-phenoxybut-1-enyl)-1,4-dioxaspiro[4,4]nonane.

(ii) Preparation of 7-(3-hydroxy-3-methyl-4-phenoxybut-1-enyl)-6-(7-trimethylsiloxyheptyl)-1,4-dioxaspiro[4,4]nonane By proceeding in a similar manner to that hereinbefore described in Example 3(iii), but replacing the 6-(7-trimethylsiloxyheptyl)-7-(3-oxooct-1-enyl)-1,4-dioxaspiro[4,4]nonane used as starting material by the appropriate quantity of 6-(7-trimethylsiloxyheptyl)-7-(3-oxo-4-phenoxybut-1-enyl)-1,4-dioxaspiro[4,4]nonane, there was prepared 7-(3-hydroxy-3-methyl-4-phenoxybut-1-enyl)-6-(7-trimethylsiloxyheptyl)-1,4-dioxaspiro[4,4]nonane.

(iii) Preparation of 7-[2-(3-hydroxy-3-methyl-4-phenoxybut-1-enyl)-5-oxocyclopentyl]heptanol By proceeding in a similar manner to that hereinbefore described in Example 5, but replacing the 7-(3-hydroxy-3-methyloct-1-enyl)-6-(7-trimethylsiloxy heptyl)-1,4-dioxaspiro[4,4]nonane used as starting material by the appropriate quantity of 7-(3-hydroxy-3-methyl-4-phenoxybut-1-enyl)-6-(7-trimethylsiloxyheptyl)-1,4- dioxaspiro[4,4]nonane, there was prepared 7-[2-(3-hydroxy-3-methyl-4-phenoxybut-1-enyl)-5-oxocyclopentyl]heptanol [Elemental analysis: Found: C, 67.5; H, 8.7%; $C_{23}H_{34}O_4:2H_2O$ requires C, 67.3, H, 9.3%; $\nu_{max}$ 975 cm$^{-1}$, 1720 cm$^{-1}$, 3400 cm$^{-1}$; N.M.R. (approximately 10% w/v solution in deuterochloroform): multiplet at 1.0–3.8δ, singlet at 1.42δ, triplet at 3.6δ, singlet at 3.85δ, multiplets at 5.7–5.9δ, 6.8–7.8δ].

The present invention includes within its scope pharmaceutical compositions which comprise at least one compound of the above-mentioned novel class of cyclopentane derivatives of general formula I together with a pharmaceutical carrier or coating. In clinical practice the novel compounds of the present invention will normally be administered orally, rectally, nasally, vaginally or parenterally.

The term "pharmaceutical composition", as used in the present specification, is meant to include compositions suitable for administration to animals, more particularly farm animals such as horses and cattle and other domestic animals such as dogs, as well as compositions suitable for administration to human beings.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharamceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult human, the doses are generally between 0.02 and 2.0 mg. by aerosol administration as bronchodilators, between 0.0002 and 2.0 mg./kg. body weight by intravenous administration, preferably by intravenous infusion at a rate of between 0.001 and 1.0 mg./kg. body weight/minute as hypotensives, between 0.001 and 0.3 mg./kg. body weight orally as inhibitors of gastric acid secretion, between 0.01 and 1.0 mg./kg. body weight by intravenous administration, preferably by intravenous infusion at a rate of between 0.02 and 20 μg./kg. body weight/minute as stimulators of uterine contraction, and between 1.0 and 50 μg./kg. body weight orally as hypocholesteraemics and hypolipidaemics, and in female mammals between 10 and 500 μg./kg. body weight administered vaginally in the control of oestrus. If necessary these doses may be repeated as and when required.

The compounds of general formula I may be administered orally as bronchodilators by any method known per se for administration by inhalation of drugs which are not themselves gaseous under normal conditions of administration. Thus, a solution of the active ingredient in a suitable pharmaceutically-acceptable solvent, for example water or aqueous ethanol, preferably in the presence of a pharmaceutically acceptable wetting agent, e.g. Tween 80, can be nebulized by a mechanical nebulizer, for example a Wright Nebulizer, to give an aerosol of finely-divided liquid particles suitable for inhalation. Advantageously, the solution to be nebulized is diluted, solutions containing from 0.2 to 20 mg., and preferably 0.2 to 5.0 mg., of active ingredient per ml. of solution being particularly suitable. Aqueous solutions may contain stabilizing agents such as sodium bisulphite and buffering agents to give an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of two constituents e.g. a mixture of dichlorodifluoromethane and dichlorotetrafluoroethane in the proportions 38:62 respectively by weight has a vapor pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents and then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.2 to 20 mg., and more particularly 0.2 to 5.0 mg., of active ingredient per ml. of solution or suspension. It is important that the pH of solutions and suspensions used, according to the present invention, to generate aerosols should be kept within the range 3 to 8 and preferable that they should be stored at or below 4° C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, wetting, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 14

7-[2-(3-Hydroxy-3-methyloct-1-enyl)-5-oxocyclopenyl]heptanol (20 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica) (200 mg.) was added and the powder obtained was machine filled into one hundred No. 2 hard gelatin capsules to give capsules each containing 200 μg. of 7-[2-(3-hydroxy-3-methyloct-1-enyl)-5-oxocyclopentyl]heptanol which, after swallowing the capsules, is released into the stomach.

EXAMPLE 15

7-[2-(3-Hydroxy-3-methyloct-1-enyl)-5-oxocyclopentyl]heptanol (20 mg.) was dissolved in absolute ethanol (4 ml.) containing Tween 80 (1% w/v) and the solution was diluted with distilled water (36 ml.) to give a solution of the active compound suitable for a plurality of doses suitable for intravenous injection.

We claim:

1. A cyclopentane derivative of the formula:

wherein $R^1$ is hydrogen, alkanoyl of 1 to 4 carbon atoms, or benzoyl, A is alkylene of 1 to 12 carbon atoms, Z is a direct bond or oxygen or sulphur, X is ethylene or trans-vinylene, Y is carbonyl or 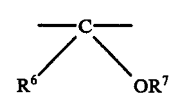 where $R^6$ is hydrogen or alkyl of 1 to 4 carbon atoms and $R^7$ is hydrogen, alkanoyl of 1 to 4 carbon atoms, or benzoyl, and $R^8$ is phenyl or naphthyl which is unsubstituted or substituted by halogen, alkyl of 1 to 6 carbon atoms, alkoxy of 1 to 6 carbon atoms, or trihalomethyl.

2. A cyclopentane derivative according to claim 1 wherein A is alkylene of 1 to 7 carbon atoms.

3. A cyclopentane derivative according to claim 1 wherein A is methylene, Z is oxygen and $R^8$ is phenyl.

4. A cyclopentane derivative according to claim 1 wherein Y represents a group of the formula:

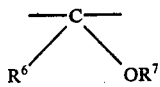  III wherein $R^6$ represents methyl and $R^7$ is as defined in claim 1.

5. A cyclopentane derivative according to claim 1 wherein $R^8$ represents phenyl.

6. A cyclopentane derivative according to claim 1 in which the group attached to the 8-position of the cyclopentane ring of formula I depicted in claim 1 is in alpha configuration and the group attached to the 12-position of the cyclopentane ring is in beta-configuration.

7. A cyclopentane derivative according to claim 1 which is 7-[2-(3-hydroxy-4-phenoxybut-1-enyl)-5-oxocyclopentyl]heptanol.

8. A cyclopentane derivative according to claim 1 which is 7-[2-(3-hydroxy-3-methyl-4-phenoxybut-1-enyl)-5-oxocyclopentyl]heptanol.

9. A cyclopentane derivative according to claim 1 which is 7-[5-(3-oxo-6-phenylhex-1-enyl)-2-oxocyclopentyl]heptanol.

10. A cyclopentane derivative according to claim 1 which is 7-[5-(3-oxo-5-phenylpent-1-enyl)-2-oxocyclopentyl]heptanol.

11. A cyclopentane derivative according to claim 1 which is 7-[5-(3-oxo-4-phenylbut-1-enyl)-2-oxocyclopentyl]heptanol.

12. A cyclopentane derivative according to claim 1 which is 7-{5-[3-oxo-4-(2-phenylethyl)oct-1-enyl]-2-oxocyclopentyl}heptanol.

* * * * *

UNITED STATES PATENT AND TRADEMARK OFFICE
CERTIFICATE OF CORRECTION

PATENT NO. : 4,088,695
DATED : May 9, 1978
INVENTOR(S) : Michael Peter Lear CATON et al It is certified that error appears in the above-identified patent and that said Letters Patent are hereby corrected as shown below:

Claim 1, please correct the formula to read as follows:

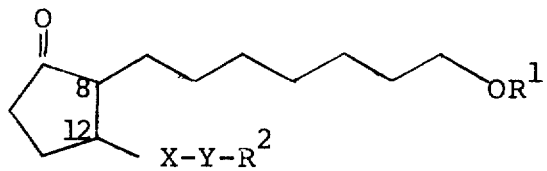

Signed and Sealed this

Seventeenth Day of April 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,088,695
DATED : May 9, 1978
INVENTOR(S) : Michael Peter Lear CATON et al It is certified that error appears in the above-identified patent and that said Letters Patent are hereby corrected as shown below:

In claim 1, column 30, please correct the first formula to read as follows:

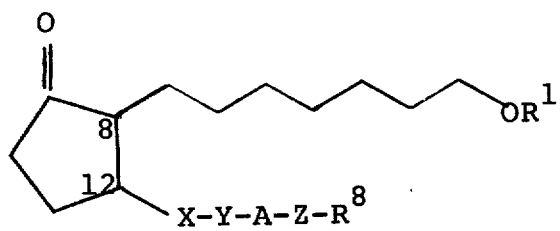

This supersedes the Certificate of Correction dated April 17, 1979.

Signed and Sealed this

Twenty-fourth Day of July 1979

[SEAL]

Attest:

Attesting Officer

LUTRELLE F. PARKER
Acting Commissioner of Patents and Trademarks